(12) United States Patent
Geneste et al.

(10) Patent No.: US 9,388,180 B2
(45) Date of Patent: Jul. 12, 2016

(54) INHIBITOR COMPOUNDS OF PHOSPHODIESTERASE TYPE 10A

(71) Applicants: Abbott GmbH & Co. KG, Wiesbaden (DE); AbbVie Inc., North Chicago, IL (US)

(72) Inventors: Hervé Geneste, Ludwigshafen (DE); Michael Ochse, Ludwigshafen (DE); Karla Drescher, Ludwigshafen (DE); Clarissa Jakob, North Chicago, IL (US); Maricel Torrent, Lake Bluff, IL (US)

(73) Assignees: AbbVie Inc., North Chicago, IL (US); Abbott GmbH & Co. KG, Wiesbaden (DE)

( * ) Notice: Subject to any disclaimer, the term of this patent is extended or adjusted under 35 U.S.C. 154(b) by 274 days.

(21) Appl. No.: 14/029,142

(22) Filed: Sep. 17, 2013

(65) Prior Publication Data
US 2014/0107126 A1    Apr. 17, 2014

Related U.S. Application Data

(60) Provisional application No. 61/702,005, filed on Sep. 17, 2012, provisional application No. 61/702,371, filed on Sep. 18, 2012.

(51) Int. Cl.
| | | |
|---|---|---|
| *C07D 491/14* | (2006.01) | |
| *C07D 495/14* | (2006.01) | |
| *C07D 498/14* | (2006.01) | |
| *C07D 513/14* | (2006.01) | |
| *A61K 31/4985* | (2006.01) | |
| *A61P 25/18* | (2006.01) | |
| *A61P 25/24* | (2006.01) | |
| *A61P 25/28* | (2006.01) | |
| *A61P 25/30* | (2006.01) | |
| *A61P 3/04* | (2006.01) | |
| *C07D 471/14* | (2006.01) | |
| *C07D 491/04* | (2006.01) | |
| *C07D 495/04* | (2006.01) | |
| *C07D 498/04* | (2006.01) | |

(52) U.S. Cl.
CPC .......... *C07D 471/14* (2013.01); *A61K 31/4985* (2013.01); *C07D 491/04* (2013.01); *C07D 491/14* (2013.01); *C07D 495/04* (2013.01); *C07D 495/14* (2013.01); *C07D 498/04* (2013.01); *C07D 498/14* (2013.01); *C07D 513/14* (2013.01)

(58) Field of Classification Search
CPC .. C07D 487/14; C07D 491/14; C07D 495/14; C07D 498/14; C07D 513/14; A61K 31/4985
USPC .......................................... 544/345; 514/250
See application file for complete search history.

(56) References Cited

U.S. PATENT DOCUMENTS

2007/0155779 A1    7/2007   Verhoest et al.

FOREIGN PATENT DOCUMENTS

| WO | 03/093499 A2 | 11/2003 |
| WO | 2005/012485 A2 | 2/2005 |

(Continued)

OTHER PUBLICATIONS

Freshney et al., Culture of Animal Cells, A Manual of Basic Technique, Alan R. Liss, Inc., 1983, New York, p. 4.*
Dermer et al., Bio/Technology, 1994, 12:320.*
Siuciak, J.A. et al., "Behavioral and neurochemical characterization of mice deficient in the phosphodiesterase-4B (PDE4B) enzyme," Psychopharmacology (2008) 197:115-126.

(Continued)

*Primary Examiner* — Venkataraman Balasubramanian
(74) *Attorney, Agent, or Firm* — Neal Gerber & Eisenberg LLP

(57) ABSTRACT

The present invention relates to compounds of the formula I, the N-oxides, tautomers, the prodrugs and the pharmaceutically acceptable salts thereof.

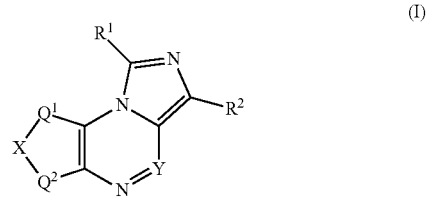

where in formula I the variables X, Y, $Q^1$, $Q^2$ have the following meanings:

X is C—$R^3$ or N;
$Q^1$ is S or O and $Q^2$ is C—$R^4$ or N and $Q^2$ is connected to X via a double bond while $Q^1$ is connected to X via a single bond; or
$Q^2$ is S or O and $Q^1$ is C—$R^4$ or N and $Q^1$ is connected to X via a double bond while $Q^2$ is connected to X via a single bond;
Y is C—$R^5$ or N;
where in formula I the variables $R^1$, $R^2$, $R^3$, $R^4$ and $R^5$ are as defined in the claims The compounds of the formula I, the N-oxides, tautomers, the prodrugs and the pharmaceutically acceptable salts thereof are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

37 Claims, No Drawings

(56) References Cited

FOREIGN PATENT DOCUMENTS

| WO | 2005/120514 | A1 | 12/2005 |
|---|---|---|---|
| WO | 2006/028957 | A1 | 3/2006 |
| WO | 2007/022280 | A1 | 2/2007 |
| WO | 2007/082546 | A1 | 7/2007 |
| WO | 2007/085954 | A2 | 8/2007 |
| WO | 2007/096743 | A1 | 8/2007 |
| WO | 2007/098169 | A1 | 8/2007 |
| WO | 2007/098214 | A1 | 8/2007 |
| WO | 2007/100880 | A1 | 9/2007 |
| WO | 2007/103370 | A2 | 9/2007 |
| WO | 2007/103554 | A1 | 9/2007 |
| WO | 2007/137819 | A1 | 12/2007 |
| WO | 2007/137820 | A1 | 12/2007 |
| WO | 2008/001182 | A1 | 1/2008 |
| WO | 2008/004117 | A1 | 1/2008 |
| WO | 2008/006372 | A1 | 1/2008 |
| WO | 2008/020302 | A2 | 2/2008 |
| WO | 2009/025823 | A1 | 2/2009 |
| WO | 2009/025839 | A2 | 2/2009 |
| WO | 2009/029214 | A1 | 3/2009 |
| WO | 2009/036766 | A1 | 3/2009 |
| WO | 2009/068246 | A2 | 6/2009 |
| WO | 2009/068320 | A1 | 6/2009 |
| WO | 2009/070583 | A1 | 6/2009 |
| WO | 2009/070584 | A1 | 6/2009 |
| WO | 2009/152133 | | 12/2009 |
| WO | 2010/054260 | A1 | 5/2010 |
| WO | 2011/008597 | A1 | 1/2011 |
| WO | 2011/012540 | | 2/2011 |

OTHER PUBLICATIONS

Schmidt et al, The Journal of Pharmacology and Experimental Therapeutics, 325, 681-690 (2008).
Nishi, The Journal of Neuroscience, 28, 10450-10471 (2008).
Seeger et al., Brain Research, 985, 113-126 (2003).
Rodefer et al., Eur. J. Neurosci., 4, 1070-1076 (2005).
Grauer et al., Journal of Pharmacology and Experimental Therapeutics, fast forward DOI 10.1124 JPET 109.155994 (2009).
Francis et al., Physiol. Rev., 91, 651-690 (2011).
Sotty et al., J. Neurochem., 109, 766-775 (2009).
Cantin et al., Bioorganic & Medicinal Chemistry Letters, 17, 2869-2873 (2007).
Chappie et al., Current Opinion in Drug Discovery & Development, 12(4), 458-467 (2009).
Diaz et al., Journal of Pharmacological and Toxicological Methods, 50, 187-199 (2004).
Blokland A., et al., "PDE Inhibition and Cognition Enhancement," Expert Opinion on Therapeutic Patents, 2012, vol. 22 (4), pp. 349-354.
Hoefgen N., et al., "Targeting PDE10A in Schizophrenia," Drugs of the Future, 2012, vol. 37 (8), pp. 577-589.
Kehler J., et al., "PDE10A Inhibitors: Novel Therapeutic Drugs for Schizophrenia," Current Pharmaceutical Design, 2011, vol. 17 (2), pp. 137-150.
Kerner B., et al., "Genome-Wide Association Study in Bipolar Patients Stratified by Co-Morbidity," PLoS ONE, 2001, vol. 6 (12), p. e28477.
Langen B., et al., "Effect of PDE10A Inhibitors on MK-801-Induced Immobility in the Forced Swim Test," Psychopharmacology, 2012, vol. 221 (2), pp. 249-259.

* cited by examiner

INHIBITOR COMPOUNDS OF PHOSPHODIESTERASE TYPE 10A

CROSS-REFERENCE TO RELATED APPLICATIONS

This is a non-provisional of U.S. patent application No. 61/702,005, filed on Sep. 17, 2012, and a non-provisional of U.S. patent application No. 61/702,371, filed on Sep. 18, 2012, the contents of all of which are incorporated herein by reference.

The present invention relates to compounds which are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

BACKGROUND OF THE INVENTION

Phosphodiesterase type 10A (hereinafter PDE10A) is a dual-substrate phosphodiesterase that can convert both cAMP to AMP and cGMP to GMP. PDE10A is highly prominent in the mammalian brain. In the rat, as well as in other mammalian species, PDE10A and the mRNA of PDE10A are highly enriched in the GABAergic medium spiny projection neurons (MSNs) of the striatal complex (caudate nucleus, nucleus accumbens, and olfactory tubercle) where the output is regulated by the effect of PDE10A on cAMP and cGMP signalling cascades (see e.g. C. J. Schmidt et al, The Journal of Pharmacology and Experimental Therapeutics 325 (2008) 681-690, A. Nishi, The Journal of Neuroscience 2008, 28, 10450-10471).

MSNs express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway. PDE10A regulation of cAMP and/or cGMP signaling in the dendritic compartment of these neurons may be involved in filtering the cortico/thalamic input into the MSN. Furthermore, PDE10A may be involved in the regulation of GABA release in the substantia nigra and globus pallidus (Seeger, T. F. et al. Brain Research, 2003, 985, 1 13-126). Inhibition of PDE10A results in striatal activation and behavioral suppression such as dampened locomotion, inhibition of conditioned avoidance response (CAR), and activity in the rat auditory gating model, suggesting that inhibitors of phosphodiesterase type 10A represent a novel class of antipsychotic agents.

The hypotheses around the physiological role of PDE10A and the therapeutic utility of PDE10A inhibitors derive in part from studies with papaverine (J. A. Siuciak et al., Psychopharmacology 2008, 197 (1) 115-126), the first extensively profiled pharmacological tool compound for this target. The PDE10A inhibitor papaverine was shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine-induced hyperactivity was insignificant (WO 03/093499). These models suggest that PDE10A inhibition has the classic antipsychotic potential that would be expected from theoretical considerations. Papaverine, however has significant limitations in this regard with relatively poor potency and selectivity and a very short exposure half-life after systemic administration. It was found that inhibition of PDE10A reverses subchronic PCP-induced deficits in attentional set-shifting in rats suggesting that PDE10A inhibitors might alleviate cognitive deficits associated with schizophrenia. (Rodefer et al., Eur. J. Neurosci., 4 (2005) 1070-1076).

The discovery of a new class of PDE10A inhibitors with improved potency, selectivity, and pharmacokinetic properties, provided an opportunity to further explore the physiology of PDE10A and the potential therapeutic utility of inhibiting this enzyme. The new class of inhibitors are exemplified by MP-10 (PF-2545920: 2-{4-[1-methylpyridine-4-yl-1-H-pyrazol-3-31y]phenoxymethyl}-quinoline) and TP-10, i.e. 2-{4-[pyridine-4-yl-1-(2,2,2-trifluoroethyl)-1-H-pyrazol-3-31y]phenoxymethyl}-quinoline. The compounds offer a therapeutic approach to the treatment of schizophrenia (see C. J. Schmidt et al., loc cit.; S. M. Grauer et al., Journal of Pharmacology and Experimental Therapeutics, fast forward DOI 10.1124 JPET 109.155994). Positive signals in rodent models of schizophrenia include the: attenuation of conditioned avoidance response (CAR), inhibition of hyperactivity caused by amphetamine-induced dopamine release or phencyclidine (PCP) mediated NMDA receptor blockade, attenuation of pharmacologically impaired social or object recognition, and antagonism of apomorphine-induced climbing. Taken together, these data suggest a broad suppression of all 3 symptoms clusters (positive symptoms, negative symptoms & cognitive dysfunctions) linked to schizophrenia (see C. J. Schmidt et al., loc cit.; S. M. Grauer et al., loc. cit).

Beyond schizophrenia, selective PDE10 inhibitors may have the potential for the treatment of Huntington's disease (S. H. Francis et al., Physiol. Rev., 91 (2011) 651-690) and they may be an therapeutic option for substance abuse disorders (F. Sotty et al., J. Neurochem., 109 (2009) 766-775). Furthermore, it has been suggested that PDE10A inhibitors may be useful for treatment of obesity and non-insulin dependent diabetes (see e.g. WO 2005/120514, WO 2005/012485, Cantin et al, Bioorganic & Medicinal Chemistry Letters 17 (2007) 2869-2873).

In summary, inhibitors of PDE10A offer a promising therapeutic approach to the treatment or prevention of neurological and psychiatric disorders, in particular schizophrenia and related disorders, including symptoms linked to schizophrenia such as cognitive dysfunction.

Several classes of compounds which are inhibitors of PDE10A have been described in the art, the recent compound groups are:

Imidazo[1,5-a]pyrido[3,2-e]pyridazines and structurally related tricyclic Imidazo[1,5-a]pyridazines—see WO 2007/137819, WO 2007/137820, WO 2009/068246, WO 2009/068320, WO 2009/070583, WO 2009/070584, WO 2010/054260 and WO 2011/008597;

4-substituted phthalazines and quinazolines WO 2007/085954, WO 2007/022280, WO 2007/096743, WO 2007/103370, WO 2008/020302, WO 2008/006372 and WO 2009/036766;

4-substituted cinnazolines—see WO 2006/028957, WO 2007/098169, WO 2007/098214, WO 2007/103554, WO 2009/025823 and WO 2009/025839;

Isoquinolines and isoquinolinones—see WO 2007/100880 and WO 2009/029214;

MP10 and MP10 like compounds: US 2007/0155779, WO 2008/001182 and WO 2008/004117; and Benzodiazepines—see WO 2007/082546.

For a further review see also T. Chappie et al. Current Opinion in Drug Discovery & Development 12(4), (2009) 458-467) and the literature cited therein.

Although some of the compounds of prior art are known to inhibit PDE10A effectively having $IC_{50}$ values of less than 50 nM, there is still an ongoing need for compounds which inhibit PDE10A. In particular, there is an ongoing need for compounds which have one of the following characteristics:

i. Selective inhibition of PDE10A, in particular vis-à-vis inhibition of other phosphodiesterases such as PDE2, PDE3 or PDE4;
ii. metabolic stability, in particular microsomal stability, e.g. measured in vitro, in liver microsomes from various species (e.g. rat or human) in human cells, such as hepatocytes;
iii. no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;
iv. a suitable solubility in water (in mg/ml);
v. suitable pharmacokinetics (time course of the concentration of the compound of the invention in plasma or in tissue, for example brain). The pharmacokinetics can be described by the following parameters: half-life, volume of distribution (in $1·kg^{-1}$), plasma clearance (in $1·h^{-1}·kg^{-1}$), AUC (area under the curve, area under the concentration-time curve (in $ng·h·l^{-1}$), oral bioavailability, (the dose-normalized ratio of AUC after oral administration and AUC after intravenous administration), the so-called brain-plasma ratio (the ratio of AUC in brain tissue and AUC in plasma);
vi. no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).
vii. high free fraction in brain, i.e. the fraction of the compound bound to proteins should be low.
viii. low lipophilicity.

BRIEF DESCRIPTION OF THE INVENTION

The present invention is thus based on the object of providing compounds which inhibit PDE10A at low concentrations.

The compounds are further intended to display at least one of the properties i. to viii. mentioned above, in particular high selectivity with regard to inhibition of PDE10A, high selectivity vis-à-vis other phosphodiesterases such as, enhanced metabolic stability, in particular microsomal stability, cytosolic stability or hepatocyte stability, low affinity to the HERG receptor, low inhibition of cytochrome P450 (CYP) enzymes, suitable solubility in water and suitable pharmacokinetics.

This object and further objects are achieved by the compounds of the general formula I described below, the N-oxides, the prodrugs, the hydrates and the tautomers thereof and the pharmaceutically suitable salts thereof:

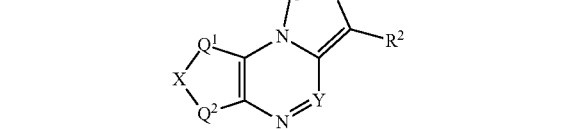

(I)

where in formula I the variables X, Y, $Q^1$, $Q^2$, $R^1$ and $R^2$ have the following meanings:

X is C—$R^3$ or N;
$Q^1$ is S or O and $Q^2$ is C—$R^4$ or N and $Q^2$ is connected to X via a double bond while $Q^1$ is connected to X via a single bond; or
$Q^2$ is S or O and $Q^1$ is C—$R^4$ or N and $Q^1$ is connected to X via a double bond while $Q^2$ is connected to X via a single bond;
Y is C—$R^5$ or N;
$R^1$ is selected from the group consisting of hydrogen, halogen, cyano, nitro, $R^{11}$, OH, $OR^{12}$, $S(O)_qR^{13}$, C(O)H, C(O)$R^{14}$, C(O)OH, C(O)$OR^{15}$, OC(O)$R^{16}$, $Y^1$—$NR^{17}R^{18}$, $Y^1$—N($R^{19}$)—$Y^3$—$NR^{17}R^{18}$, $Y^1$—N($R^{19}$)—$Y^2$—$R^{15a}$ and a moiety $Z^1$—$Ar^1$;
$R^2$ is selected from the group consisting of hydrogen, halogen, cyano, nitro, $R^{21}$, OH, $OR^{22}$, $S(O)_qR^{23}$, C(O)H, C(O)$R^{24}$, C(O)OH, C(O)$OR^{25}$, OC(O)$R^{26}$, $Y^1$—$NR^{27}R^{28}$, $Y^1$—N($R^{29}$)—$Y^3$—$NR^{27}R^{28}$, $Y^1$—N($R^{19}$)—$Y^2$—$R^{25a}$ and a moiety $Z^2$—$Ar^2$;
provided that at least one of $R^1$ and $R^2$ is different from hydrogen;
$R^3$ is selected from the group consisting of hydrogen, halogen, cyano, nitro, $R^{31}$, $OR^{32}$, $S(O)_qR^{33}$, C(O)H, C(O)$R^{34}$, C(O)OH, C(O)$OR^{35}$, OC(O)$R^{36}$, $Y^1$—$NR^{37}R^{38}$, $Y^1$—N($R^{39}$)—$Y^3$—$NR^{37}R^{38}$, $Y^1$—N($R^{39}$)—$Y^2$—$R^{35a}$ and a moiety $Z^3$—$Ar^3$;
$R^4$ is selected from the group consisting of hydrogen, halogen, cyano, nitro, $R^{41}$, $OR^{42}$, $S(O)_qR^{43}$, C(O)H, C(O)$R^{44}$, C(O)OH, C(O)$OR^{45}$, OC(O)$R^{46}$, $Y^1$—$NR^{47}R^{48}$, $Y^1$—N($R^{49}$)—$Y^3$—$NR^{47}R^{48}$, $Y^1$—N($R^{49}$)—$Y^2$—$R^{45a}$ and a moiety $Z^4$—$Ar^4$;
$R^5$ is selected from the group consisting of hydrogen, halogen, cyano, nitro, $R^{51}$, $OR^{52}$, $S(O)_qR^{53}$, C(O)H, C(O)$R^{54}$, C(O)OH, C(O)$OR^{55}$, OC(O)$R^{56}$, $Y^1$—$NR^{57}R^{58}$, $Y^1$—N($R^{59}$)—$Y^3$—$NR^{57}R^{58}$, $Y^1$—N($R^{59}$)—$Y^2$—$R^{55a}$ and a moiety $Z^5$—$Ar^5$;
$R^{11}$, $R^{12}$, $R^{13}$, $R^{14}$, $R^{15}$, $R^{16}$, $R^{21}$, $R^{22}$, $R^{23}$, $R^{24}$, $R^{25}$, $R^{26}$, $R^{31}$, $R^{32}$, $R^{33}$, $R^{34}$, $R^{35}$, $R^{36}$, $R^{41}$, $R^{42}$, $R^{43}$, $R^{44}$, $R^{45}$, $R^{46}$, $R^{51}$, $R^{52}$, $R^{53}$, $R^{54}$, $R^{55}$, and $R^{56}$, independently of each other, are selected from the group consisting of $C_1$-$C_8$-alkyl, $C_2$-$C_8$-alkenyl, $C_2$-$C_8$-alkynyl, $C_3$-$C_8$-cycloalkyl, $C_5$-$C_8$-cycloalkenyl, $C_3$-$C_8$-cycloalkyl-$C_1$-$C_4$-alkyl, where the 6 aforementioned substituents may be unsubstituted, partially or completely halogenated or carry 1, 2 or 3 radicals $R^y$, and C-bound 5- to 8-membered heterocyclyl, which is saturated or partially unsaturated and has 1 or 2 heteroatom moieties as ring members, which are selected from the group consisting of O, N, S, S(O), S(O)$_2$ or N—$R^x$, where heterocyclyl is unsubstituted or carries 1, 2, 3 or 4 radicals $R^{yy}$;

$R^{17}$ and $R^{18}$, independently of each other, are selected from the group consisting of hydrogen, tri-$C_1$-$C_4$-alkylsilyl, $C_1$-$C_8$-alkyl, $C_2$-$C_8$-alkenyl, $C_2$-$C_8$-alkynyl, $C_3$-$C_8$-cycloalkyl, $C_5$-$C_8$-cycloalkenyl, $C_3$-$C_8$-cycloalkyl-$C_1$-$C_4$-alkyl, where the 6 aforementioned substituents may be unsubstituted, partially or completely halogenated or carry 1, 2 or 3 radicals $R^y$, $C_1$-$C_8$-alkylcarbonyl, $C_1$-$C_4$-haloalkylcarbonyl, $C_1$-$C_8$-alkylsulfonyl, $C_1$-$C_4$-haloalkylsulfonyl, and C-bound 5- to 8-membered heterocyclyl, which is saturated or partially unsaturated and has 1 or 2 heteroatom moieties as ring members, which are selected from the group consisting of O, N, S, S(O), S(O)$_2$ or N—$R^x$, where heterocyclyl is unsubstituted or carries 1, 2, 3 or 4 radicals $R^{yy}$ or $R^{17}$ and $R^{18}$, together with the nitrogen atom, to which they are attached, form an N-bound 5- to 8-membered heterocyclyl, which is saturated, partially unsaturated or aromatic and in addition to the nitrogen atom may have 1 or 2 further heteroatom moieties as ring members, which are selected from the group consisting of O, N, S, S(O), S(O)$_2$ or N—$R^x$, where heterocyclyl is unsubstituted or carries 1, 2, 3 or 4 radicals $R^{yy}$;

$R^{19}$, $R^{29}$, $R^{39}$, $R^{49}$ and $R^{59}$, independently of each other, are hydrogen or have one of the meanings given for $R^{11}$;

$R^{27}$ and $R^{28}$ are as defined for $R^{17}$ and $R^{18}$;
$R^{37}$ and $R^{38}$ are as defined for $R^{17}$ and $R^{18}$;
$R^{47}$ and $R^{48}$ are as defined for $R^{17}$ and $R^{18}$;
$R^{57}$ and $R^{58}$ are as defined for $R^{17}$ and $R^{18}$;

$R^{15a}$, $R^{25a}$, $R^{35a}$, $R^{45a}$ and $R^{55a}$, independently of each other, have one of the meanings given for $R^{11}$;

q is 0, 1 or 2

$Ar^1$, $Ar^2$, $Ar^3$, $Ar^4$ and $Ar^5$, independently of each other, are selected from the group consisting of aryl, monocyclic 5- or 6-membered hetaryl and bicyclic 9 or 10 membered hetaryl, where hetaryl has 1, 2 or 3 heteroatoms as ring members which are selected from O, S and N, where aryl and hetaryl are unsubstituted or may carry 1, 2, 3 or 4 identical or different substituents $R^{Ar}$;

$Y^1$ is a single bond, $C_1$-$C_4$-alkylene, $Y^5$—O—$Y^6$, $Y^5$—S(O)$_q$—$Y^6$, $Y^5$—C(O)—$Y^6$, $Y^5$—C(S)—$Y^6$, $Y^5$—C(O)O—$Y^6$, $Y^5$—OC(O)—$Y^6$, or $Y^5$—N($R^z$)—$Y^4$;

$Y^2$ is a single bond, $C_1$-$C_4$-alkylene, $Y^5$—O—$Y^6$, $Y^5$—S(O)$_q$—$Y^6$, $Y^5$—C(O)—$Y^6$, $Y^5$—C(S)—$Y^6$, $Y^5$—C(O)O—$Y^6$, $Y^5$—OC(O)—$Y^6$, or $Y^5$—N($R^z$)—$Y^4$;

$Y^3$ is a single bond, $C_1$-$C_4$-alkylene, $Y^5$—S(O)$_q$—$Y^6$, $Y^5$—C(O)—$Y^6$, $Y^5$—C(S)—$Y^6$, $Y^5$—C(O)O—$Y^6$, or $Y^5$—OC(O)—$Y^6$;

$Y^4$ is a $C_1$-$C_4$-alkylene, $Y^5$—S(O)$_q$—$Y^6$, $Y^5$—C(O)—$Y^6$, $Y^5$—C(S)—$Y^6$, $Y^5$—C(O)O—$Y^6$, or $Y^5$—OC(O)—$Y^6$;

$Y^5$ is a single bond or $C_1$-$C_4$-alkylene;
$Y^6$ is a single bond or $C_1$-$C_4$-alkylene;

$Z^1$, $Z^2$, $Z^3$, $Z^4$ and $Z^5$ are independently of each other selected from a single bond, $C_1$-$C_4$-alkylene, $Y^5$—O—$Y^6$, $Y^5$—S(O)$_q$—$Y^6$, $Y^5$—C(O)—$Y^6$, $Y^5$—C(S)—$Y^6$, $Y^5$—C(O)O—$Y^6$, $Y^5$—OC(O)—$Y^6$ and $Y^5$—N($R^z$)—$Y^4$;

$R^x$ is selected from the group consisting of hydrogen, $C_1$-$C_8$-alkyl, $C_2$-$C_8$-alkenyl, $C_2$-$C_8$-alkynyl, $C_3$-$C_8$-cycloalkyl, $C_5$-$C_8$-cycloalkenyl, $C_3$-$C_8$-cycloalkyl-$C_1$-$C_4$-alkyl, where the 6 aforementioned substituents may be unsubstituted, partially or completely halogenated or carry 1, 2 or 3 radicals $R^y$, phenyl and phenyl-$C_1$-$C_4$-alkyl, where phenyl and phenyl-$C_1$-$C_4$-alkyl are unsubstituted or may carry 1, 2, 3 or 4 radicals $R^{yy}$;

$R^y$ is selected from the group consisting of cyano, OH, $OR^{y2}$, $S(O)_qR^{y3}$, C(O)H, C(O)$R^{y4}$, C(O)OH, C(O)$OR^{y5}$, OC(O)$R^{y6}$, $Y^1$—$NR^{y7}R^{y8}$, $Y^1$—N($R^{y9}$)—$Y^3$—$NR^{y7}R^{y8}$ and $Y^1$—N($R^{y9}$)—$Y^2$—$R^{y0}$;

$R^{yy}$ is selected from the group consisting of cyano, halogen, $R^{y1}$, OH, $OR^{y2}$, $S(O)_qR^{y3}$, C(O)H, C(O)$R^{y4}$, C(O)OH, C(O)$OR^{y5}$, OC(O)$R^{y6}$, $Y^1$—$NR^{y7}R^{y8}$, $Y^1$—N($R^{y9}$)—$Y^3$—$NR^{y7}R^{y8}$ and $Y^1$—N($R^{y9}$)—$Y^2$—$R^{y0}$;

$R^{y0}$, $R^{y2}$, $R^{y3}$, $R^{y4}$, $R^{y5}$ and $R^{y6}$, independently of each other, are selected from the group consisting of $C_1$-$C_8$-alkyl, $C_2$-$C_8$-alkenyl, $C_2$-$C_8$-alkynyl, $C_3$-$C_8$-cycloalkyl, $C_5$-$C_8$-cycloalkenyl, $C_3$-$C_8$-cycloalkyl-$C_1$-$C_4$-alkyl, and C-bound 5- to 8-membered heterocyclyl, which is saturated or partially unsaturated and has 1 or 2 heteroatom moieties as ring members, which are selected from the group consisting of O, N, S, S(O), S(O)$_2$, NH or N—($C_1$-$C_4$-alkyl);

$R^{y7}$ and $R^{y8}$ are as defined for $R^{y0}$ or, together with the nitrogen atom, to which they are attached, form an N-bound 5- to 8-membered heterocyclyl, which is saturated or partially unsaturated and in addition to the nitrogen atom may have 1 or 2 further heteroatom moieties as ring members, which are selected from the group consisting of O, N, S, S(O), S(O)$_2$, NH or N—($C_1$-$C_4$-alkyl), where heterocyclyl is unsubstituted or carries 1, 2, 3 or 4 radicals selected from $C_1$-$C_4$-alkyl;

$R^{y9}$ is hydrogen or has one of the meanings given for $R^{y0}$;

$R^{Ar}$ is selected from the group consisting of halogen, cyano, nitro, OH, C(O)NH$_2$, $R^{Ar1}$, $OR^{Ar2}$, $S(O)_qR^{Ar3}$, C(O)H, C(O)$R^{Ar4}$, C(O)OH, C(O)$OR^{Ar5}$, OC(O)$R^{Ar6}$, $Y^1$—$NR^{Ar7}R^{Ar8}$, $Y^1$—N($R^{Ar9}$)—$Y^3$—$NR^{Ar7}R^{Ar8}$, $Y^1$—N($R^{Ar9}$)—$Y^2$—$R^{Ar0}$, where $R^{Ar0}$, $R^{Ar1}$, $R^{Ar2}$, $R^{Ar3}$, $R^{Ar4}$, $R^{Ar5}$ and $R^{Ar6}$ have one of the meanings given for $R^{11}$, $R^{Ar7}$ and $R^{Ar8}$ are as defined for $R^{17}$ and $R^{18}$, and $R^{Ar9}$ has one of the meanings given for $R^{19}$;

$R^z$ has one of the meanings given for $R^x$;

the N-oxides, tautomers, the prodrugs and the pharmaceutically acceptable salts thereof.

The present invention therefore relates to the compounds of the general formula I, the N-oxides, the tautomers and the hydrates thereof, the pharmaceutically acceptable salts of the compounds of formula I, the prodrugs of the compounds of formula I and the pharmaceutically acceptable salts of said N-oxides, prodrugs, tautomers or hydrates of the compounds of formula I. The present invention in particular relates to the compounds of the general formula I and to their pharmaceutically acceptable salts.

The present invention also relates to the compounds of the general formula I, the N-oxides, the tautomers and the hydrates thereof, the pharmaceutically acceptable salts of the compounds of formula I, the prodrugs of the compounds of formula I and the pharmaceutically acceptable salts of said N-oxides, prodrugs, tautomers or hydrates of the compounds of formula I for the use in the treatment of a medical disorder, selected from neurological and psychiatric disorders which can be treated by modulation of phosphodiesterase type 10.

The present invention also relates to the compounds of the general formula I, the N-oxides, the tautomers and the hydrates thereof, the pharmaceutically acceptable salts of the compounds of formula I, the prodrugs of the compounds of formula I and the pharmaceutically acceptable salts of said N-oxides, prodrugs, tautomers or hydrates of the compounds of formula I for the use in the treatment of drug abuse in a mammalian.

The compounds of the formula I, their pharmaceutically acceptable salts, their N-oxides, their prodrugs, their hydrates and their tautomers and the pharmaceutically acceptable salts of said N-oxides, prodrugs, tautomers or hydrates effectively inhibit PDE10A even at low concentrations. They are additionally distinguished by a high selectivity in relation to the inhibition of the PDE10A vis-à-vis inhibition of other phosphodiesterase, such as PDE2, PDE3 or PDE4. The compounds of the invention may additionally have one or more of the above mentioned properties ii. to viii.

The compounds of the formula I, their pharmaceutically acceptable salts, their N-oxides, their prodrugs, their hydrates and their tautomers and the pharmaceutically acceptable salts of said N-oxides, prodrugs, tautomers or hydrates are therefore particularly suitable for treating disorders and conditions in creatures, especially human creatures, which can be treated or controlled by inhibition of phosphodiesterase type 10A.

The invention therefore also relates to the use of the compounds of the formula I, their N-oxides, their tautomers, their hydrates and their pharmaceutically acceptable salts and the pharmaceutically acceptable salts of said N-oxides, prodrugs, tautomers or hydrates for the manufacture of a medicament, in particular of a medicament which is suitable for the treatment of a disorder or a condition which can be treated by inhibition of phosphodiesterase type 10A.

The invention further relates to a medicament, in particular a medicament which is suitable for the treatment of a disorder or a condition which can be treated by inhibition of phosphodiesterase type 10A. The medicament comprises at least one compound of the formula I, as described herein, or an N-oxide, a tautomer, or a hydrate or a prodrug of said compound I, or a pharmaceutically acceptable salt of the compound of the formula I or a pharmaceutically acceptable salt of the N-oxide, the tautomer, the hydrate or the prodrug of compound of the formula I.

DETAILED DESCRIPTION OF THE INVENTION

The terms "compound of the formula I" and "compounds I" are used as synonyms.

The term "prodrugs" means compounds which are metabolized in vivo to the compounds I of the invention. Typical examples of prodrugs are described in C. G. Wermuth (editor): The Practice of Medicinal Chemistry, Academic Press, San Diego, 1996, pages 671-715. These include for example phosphates, carbamates, amino acids, esters, amides, peptides, ureas and the like. Suitable prodrugs in the present case may be for example derivatives of those compounds I carrying an OH or $NH_2$-group, where the OH or $NH_2$-group forms an ester/amide/peptide linkage, i.e. where one of the hydrogen atoms of the OH or $NH_2$-group is substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an acyl group derived from an amino acid, e.g. glycine, alanine, serine, phenylalanine and the like, which is linked to the oxygen or nitrogen of the OH or $NH_2$-group via the carbonyl group of the amino acid. Further suitable prodrugs are alkylcarbonyloxyalkyl carbonates or carbamates of compounds I carrying an OH- or $NH_2$-group in which one of the hydrogen atoms of the OH- or $NH_2$-group has been replaced by a group of the formula —C(=O)—O—$CHR^p$—O—C(=O)—$R^q$ in which $R^p$ and $R^q$ are independently of one another $C_1$-$C_4$-alkyl. Such carbonates and carbamates are described for example in J. Alexander, R. Cargill, S. R. Michelson, H. Schwam, J. Medicinal Chem. 1988, 31(2), 318-322. These groups can then be eliminated under metabolic conditions and result in compounds I. Therefore, said prodrugs and their pharmaceutically acceptable salts are also part of the invention.

The term "pharmaceutically acceptable salts" refers to cationic or anionic salts compounds, wherein the counter ion is derived from pharmaceutically acceptable non-toxic bases or acids including inorganic or organic bases and inorganic or organic acids.

When the compound of formula I or its prodrug, tautomer, hydrate or N-oxide is acidic, salts may be prepared from pharmaceutically acceptable non-toxic bases, including inorganic and organic bases. Salts derived from inorganic bases include salts, wherein the counter ion is aluminium, ammonium, calcium, copper, ferric, ferrous, lithium, magnesium, manganic, manganous, potassium, sodium, zinc ion and the like. Particularly preferred are the ammonium, calcium, magnesium, potassium, and sodium ions. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of formula I or its prodrug, tautomer, hydrate or N-oxide is basic, salts may be prepared from pharmaceutically acceptable non-toxic acids, including inorganic and organic acids. Such acids include acetic, trifluoroacetic acid, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of formula I are meant to also include the pharmaceutically acceptable salts.

The compounds of the invention may be in the form of a mixture of diastereomers, or of a mixture of diastereomers in which one of the two diastereomers is enriched, or of essentially diastereomerically pure compounds (diastereomeric excess de>90%). The compounds are preferably in the form of essentially diastereomerically pure compounds (diastereomeric excess de>90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee>90%). However, the compounds of the invention are frequently prone to racemization in relation to the stereochemistry of the carbon atom which carries the radical $R^1$, so that mixtures are frequently obtained in relation to this carbon atom, or compounds which exhibit a uniform stereochemistry in relation to this C atom form mixtures under physiological conditions. However, in relation to other stereocenters and the occurrence, associated therewith, of enantiomers and diastereomers, it is preferred to employ the compounds enantiomerically pure or diastereomerically pure.

The present invention moreover relates to compounds as defined herein, wherein one or more of the atoms depicted in formula I have been replaced by a stable isotope (e.g., hydrogen by deuterium, $^{12}C$ by $^{13}C$, $^{14}N$ by $^{15}N$, $^{16}O$ by $^{18}O$) or by an instable isotope (e.g. $^{12}C$ by $^{11}C$, $^{16}O$ by $^{15}O$, $^{19}F$ by $^{18}F$), preferably by a stable isotope, or enriched with regard to said isotope beyond the natural level. Of course, the compounds according to the invention contain more of the respective isotope than this naturally occurs and thus is anyway present in the compounds I.

The compounds of the formula I and their salts in the solid form may exist in more than one crystal structure (polymorphism), and may also be in the form of hydrates or other solvates. The present invention includes any polymorph of the compound I or its salt as well as any hydrate or other solvate.

In the context of the present description, unless stated otherwise, the terms "alkyl", "alkenyl", "alkynyl", "alkoxy", "alkenyloxy", "haloalkyl", "haloalkoxy", "cycloalkyl", "halogenated cycloalkyl", "cycloalkenyl", "halogenated cycloalkenyl", "alkylene", "alkanediyl", "heterocyclyl", "hetaryl", "aryl" and radicals derived therefrom, such as "hydroxylalkyl", "alkoxylalkyl", "alkoxyalkoxy", "cycloalkylalkyl", "halogenated cycloalkylalkyl" and "hetarylalkyl" represent groups of individual radicals. The groups of noncyclic radicals "alkyl", "alkenyl", "alkynyl", "alkoxy", "haloalkyl", "haloalkoxy", "alkylene", "alkanediyl", and the groups of radicals derived therefrom always include both unbranched and branched "alkyl", "alkenyl", "alkynyl", "alkoxy", "haloroalkyl", "haloroalkoxy", "alkylene" and "alkanediyl", respectively.

The prefix $C_n$-$C_m$- indicates the respective number of carbons in the hydrocarbon unit. Unless indicated otherwise, fluorinated substituents preferably have one to five identical or different fluorine atoms.

The term "halogen" designates in each case, fluorine, bromine, chlorine or iodine, specifically fluorine, chlorine or bromine.

The term "partially or completely halogenated" indicates that at least on, e.g. 1, 2, 3, 4, 5 or 6 of the hydrogen atoms or all of the hydrogen atoms of the respective moiety are replaced by halogen atoms, in particular by fluorine atoms Examples of other meanings are:

Alkyl, and the alkyl moieties for example in alkylcarbonyl, alkylsulfanyl, alkylsulfonyl, alkylsulfanylalkyl and alkylsulfaylalkoxy: saturated, straight-chain or branched hydrocarbon radicals having one or more C atoms, e.g. 1 to 10, 1 to 8, 1 to 6 or 1 to 4 carbon atoms. Examples of $C_1$-$C_4$-alkyl are methyl, ethyl, propyl, 1-methylethyl, n-butyl, 1-methylpropyl, 2-methylpropyl and 1,1-dimethylethyl. $C_1$-$C_6$-alkyl are, apart those mentioned for $C_1$-$C_4$-alkyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Examples for $C_1$-$C_8$-alkyl or $C_2$-$C_{10}$-alkyl are, apart those mentioned for $C_1$-$C_6$-alkyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, n-octyl, 1-methyloctyl, 2-methylheptyl, 1-ethylhexyl, 2-ethylhexyl, 1,2-dimethylhexyl and 1-propylpentyl, 2-propylpentyl.

Haloalkyl and the Haloalkyl moieties for example in haloalkylsulfonyl: an alkyl radical having ordinarily 1 to 4 C atoms, in particular 1 or 2 C-atoms ($C_1$-$C_2$-fluoroalkyl) as mentioned above, whose hydrogen atoms are partly or completely replaced by halogen atoms, in particular by fluorine atoms such as fluoromethyl, difluoromethyl, trifluoromethyl, 2-fluoroethyl, 2,2-difluoroethyl, 2,2,2-trifluoroethyl, pentafluoroethyl, 2-fluoro-1-methylethyl, 2,2-difluoro-1-methylethyl, 2,2-trifluoro-1-methylethyl, 2-fluoropropyl, 3-fluoropropyl, 2,2-difluoropropyl, 2,3-difluoropropyl, 3,3,3-trifluoropropyl, 2,3,3,3-pentafluoropropyl, heptafluoropropyl, 1-(fluoromethyl)-2-fluoroethyl, 4-fluorobutyl, and nonafluorobutyl.

Cycloalkyl, and the cycloalkyl moieties for example in cycloalkoxy, cycloalkyl-$C_1$-$C_4$-alkyl or cycloalkyl-$C_1$-$C_4$-alkoxy:monocyclic, saturated hydrocarbon groups having three or more C atoms, e.g. 3, 4, 5, 6, 7 or 8 carbon ring members, such as cyclopropyl, cyclobutyl, cyclopentyl, cyclohexyl and cycloheptyl.

Halogenated cycloalkyl, and the halogenated cycloalkyl moieties for example in halogenated cycloalkoxy or halogenated cycloalkyl-$C_1$-$C_4$-alkyl:monocyclic, saturated hydrocarbon groups having three or more C atoms, e.g. 3, 4, 5, 6, 7 or 8 carbon ring members, such as cyclopropyl, cyclobutyl, cyclopentyl, cyclohexyl and cycloheptyl, wherein at least one, e.g. 1, 2, 3, 4, 5 or 6 or all of the hydrogen atoms are replaced by halogen atoms, in particular by fluorine atoms, examples including 1-fluorocyclopropyl, 2-fluorocyclopropyl, 2,2-difluorocyclopropyl, 1,2-difluorocyclopropyl, 2,3-difluorocyclopropyl, etc.

Cycloalkenyl: a mono-unsaturated monocyclic hydrocarbon groups having 5- or more C atoms, e.g. 5, 6, 7 or 8 carbon ring members, such as 1-cyclopenten-1-yl, 3-cyclopenten-1-yl, 4-cyclopenten-1-yl, 1-cyclohexen-1-yl, 3-cyclohexen-1-yl, 4-cyclohexen-1-yl, 1-cyclohepten-1-yl, 3-cyclohepten-1-yl, 4-cyclohepten-1-yl, 5-cyclohepten-1-yl, 1-cycloocten-1-yl, 2-cycloocten-1-yl, 3-cycloocten-1-yl, 4-cycloocten-1-yl and 5-cycloocten-1-yl.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethyl, cyclohexylmethyl, 1-cyclopropylethyl, 1-cyclobutylethyl, 1-cyclopentylethyl, 1-cyclohexylethyl, 2-cyclopropylethyl, 2-cyclobutylethyl, 2-cyclopentylethyl or 2-cyclohexylethyl.

Halogenated cycloalkylalkyl: a halogenated, in particular a fluorinated cycloalkyl radical as defined above which is linked via an alkylene group, in particular via a methylene, 1,1-ethylene or 1,2-ethylene group, e.g. 1-fluorocyclopropylmethyl, 2-fluorocyclopropylmethyl, 2,2-difluorocyclopropylmethyl, 1,2-difluorocyclopropylmethyl, 2,3-difluorocyclopropylmethyl, 1-(1-fluorocyclopropyl)ethyl, 1-(2-fluorocyclopropyl)ethyl, 1-(2,2-difluorocyclopropyl)ethyl, 1-(1,2-difluorocyclopropyl)ethyl, 1-(2,3-difluorocyclopropyl)ethyl, 2-(1-fluorocyclopropyl)ethyl, 2-(2-fluorocyclopropyl)ethyl, 2-(2,2-difluorocyclopropyl)ethyl, 2-(1,2-difluorocyclopropyl)ethyl or 2-(2,3-difluorocyclopropyl)ethyl.

Alkenyl, and alkenyl moieties for example in alkenyloxy: monounsaturated, straight-chain or branched hydrocarbon radicals having two or more C atoms, e.g. 2 to 8, especially 2 to 4 carbon atoms and one C=C-double bond in any position, e.g. $C_2$-$C_4$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl.

Alkynyl, and alkenyl moieties for example in alkynyloxy: monounsaturated, straight-chain or branched hydrocarbon radicals having two or more C atoms, e.g., e.g. 2 to 8, especially 2 to 6 carbon atoms and one C≡C-triple bond in any position, e.g. $C_2$-$C_4$-alkenyl such as ethynyl, 1-propynyl, 2-propynyl, 1-butynyl, 2-butynyl, 3-butynyl, 1-methyl-2-propynyl, 1-methyl-2-butynyl and 2-methyl-3-butynyl.

Alkoxy or alkoxy moieties for example in alkoxyalkyl and alkoxyalkoxy:

an alkyl radical as defined above having preferably 1 to 4 C atoms, which is connected to the remainder of the molecule via an O atom: e.g. methoxy, ethoxy, n-propoxy, 1-methylethoxy, butoxy, 1-methylpropoxy, 2-methylpropoxy or 1,1-dimethylethoxy.

Haloalkoxy: alkoxy as described above, in which the hydrogen atoms of these groups are partly or completely replaced by halogen atoms, in particular by fluorine atoms, i.e. for example $C_1$-$C_4$-fluoroalkoxy, in particular $C_1$-$C_2$-fluoroalkoxy, such as fluoromethoxy, difluoromethoxy, trifluoromethoxy, 2-fluoroethoxy, 2,2-difluoroethoxy, 2,2,2-trifluoroethoxy, pentafluoroethoxy, 2-fluoropropoxy, 3-fluoropropoxy, 2,2-difluoropropoxy, 2,3-difluoropropoxy, 3,3,3-trifluoropropoxy, 2,2,3,3,3-pentafluoropropoxy, heptafluoropropoxy, 1-(fluoromethyl)-2-fluoroethoxy, specifically fluoromethoxy, difluoromethoxy, trifluoromethoxy, 2-fluoroethoxy, or 2,2,2-trifluoroethoxy.

Hydroxyalkyl: an alkyl radical ordinarily having 1 to 4 C atoms, in which one hydrogen atom is replaced by an OH radical. Examples thereof are $CH_2$—OH, 1-hydroxyethyl, 2-hydroxyethyl, 1-hydroxypropyl, 2-hydroxypropyl, 1-methyl-1-hydroxyethyl, 1-methyl-2-hydroxyethyl, 3-hydroxypropyl, 2-hydroxybutyl, 3-hydroxybutyl, 4-hydroxybutyl, 1-methyl-2-hydroxypropyl, 1,1-dimethyl-2-hydroxyethyl, 1-methyl-1-hydroxypropyl etc.

Alkoxyalkyl: an alkyl radical ordinarily having 1 to 4 C atoms, in which one hydrogen atom is replaced by an alkoxy radical ordinarily having 1 to 4 C atoms. Examples thereof are $CH_2$—$OCH_3$, $CH_2$—$OC_2H_5$, n-propoxymethyl, $CH_2$—OCH$(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkoxyalkoxy: an alkoxyalkyl radical as defined above ordinarily having 1 to 4 C atoms both in the alkoxy and the alkyl moiety which is connected to the remainder of the molecule via an O atom: Examples thereof are $OCH_2$—$OCH_3$, $OCH_2$—$OC_2H_5$, n-propoxymethoxy, $OCH_2$—OCH$(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, etc.

"Alkylen" or "Alkanediyl", respectively: a saturated hydrocarbon chain having ordinarily from 1 to 4 carbon atoms, such as methylen (—$CH_2$—), 1,2-ethylen (—$CH_2CH_2$—), 1,1-ethandiyl (—CH($CH_3$)—), 1,2-propandiyl, 1,3-propandiyl, 1,4-butandiyl, 1,2-butandiyl, 1,3-butandiyl, 1-methyl-1,2-propandiyl, 2-methyl-1,3-propandiyl, 1-methyl-1,1-ethandiyl, 1-methyl-1,2-propandiyl etc.

Aryl: an monocyclic or fused bi- or tricyclic carbocyclic radical having at least one, e.g. 1, 2 or 3 fused phenyl rings, or one or two fused phenyl rings and 1 or two fused saturated carbocyclic rings, examples being phenyl, naphthtyl, fluorenyl, indanyl, and indenyl.

Heterocyclyl: a heterocyclic radical which may be saturated or partly unsaturated and which may be a monocyclic heterocyclic radical ordinarily having 3, 4, 5, 6, 7 or 8 ring atoms or a heterobicyclic radical ordinarily having 7, 8, 9 or 10 ring atoms, where ordinarily 1, 2, 3 or 4, in particular 1, 2 or 3, of the ring atoms are heteroatoms such as N, S or O, or heteroatom groups such as S(=O) or S(=O)$_2$ besides carbon atoms as ring members.

Examples of saturated heteromonocycles are in particular:

Saturated heteromonocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:

C-bonded, 3- or 4-membered saturated rings such as 2-oxiranyl, 2-oxetanyl, 3-oxetanyl, 2-aziridinyl, 3-thiethanyl, 1-azetidinyl, 2-azetidinyl.

C-bonded, 5-membered saturated rings such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

C-bonded, 6-membered saturated rings such as: tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

N-bonded, 5-membered saturated rings such as:
tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

N-bonded, 6-membered saturated rings such as:
piperidin-1-yl, hexahydropyrimidin-1-yl, hexahydropyrazin-1-yl, hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

Unsaturated heteromonocyclic radicals which ordinarily have 4, 5, 6 or 7 ring atoms, where ordinarily 1, 2 or 3 of the ring atoms are heteroatoms such as N, S or O, besides carbon atoms as ring members. These include for example:

C-bonded, 5-membered, partially unsaturated rings such as:
2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as:
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-4-yl, 4H-5,6-dihydro-1,3-oxazin-2-yl, 4H-5,6-dihydro-1,3-oxazin-4-yl, 4H-5, 6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as: 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as: 1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Hetaryl: a 5- or 6-membered aromatic heteromonocyclic radical (also termed 5- or 6-membered monocyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members and a 8-, 9- or 10-membered aromatic heterobicyclic radical (also termed 8-, 9- or 10-membered bicyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members: for example C-bonded, 5-membered monocyclic hetaryl having 1, 2 or 3 or 4 nitrogen atoms or a heteroatom selected from oxygen and sulfur and, if appropriate, having 1, 2 or 3 nitrogen atoms as ring members, such as:

2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered monocyclic hetaryl having 1, 2 or 3 nitrogen atoms as ring members, such as:

pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:

pyrrol-1-yl, pyrazol-1-yl, imidazol-1-yl, 1,2,3-triazol-1-yl, 1,2,4-triazol-1-yl, tetrazol-1-yl.

bicyclic 8-, 9-10-membered hetaryl, hetaryl which has one of the aforementioned 5- or 6-membered heteroaromatic rings and a further aromatic carbocycle or 5- or 6-membered heterocycle fused thereto, for example a fused benzene, thiophene, furane, pyrrole, pyrazole, imidazole, pyridine or pyrimidine ring. These bicyclic hetaryl include for example quinolinyl, isoquinolinyl, cinnolinyl, indolyl, indolizynyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl.

Hetarylalkyl: a hetaryl radical as defined above which is linked via an alkylene group, in particular via a methylene, 1,1-ethylene or 1,2-ethylene group, to the remainder of the molecule.

The expression "optionally substituted" in the context of the present invention means that the respective moiety is unsubstituted or has 1, 2 or 3, in particular 1, substituents which are selected from halogen, $C_1$-$C_4$-alkyl, $C_1$-$C_4$-haloalkyl, OH, SH, CN, $CF_3$, O—$CF_3$, COOH, O—$CH_2$—COOH, $C_1$-$C_6$-alkoxy, $C_1$-$C_4$-haloalkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2$NH-phenyl, $SO_2$-phenyl, NH—$SO_2$-phenyl, NH—CO-phenyl, CONH-hetaryl, $SO_2$NH-hetaryl, NH—$SO_2$-hetaryl and NH—CO-hetaryl, where hetaryl in the for last mentioned radicals is 5- or 6-membered hetaryl having one heteroatom selected from O, S and N as ring member and optionally one further nitrogen atom as ring member, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

In relation to their use as inhibitors of PDE10A, the variables X, Y, $Q^1$, $Q^2$, $R^1$ and $R^2$ in formula I preferably have the following meanings, where these represent, both considered on their own and in combination with at least one other or all, special embodiments of the compounds of the formula I:

In particular groups of embodiments, one of X, $Q^1$ and $Q^2$ is N, i.e. the moiety -$Q^1$-X-$Q^2$- forms a chain of the following formulae: —N=C($R^3$)—O—, —N=C($R^3$)—S—, —C($R^4$)=N—O—, —C($R^4$)=N—S—, —O—C($R^3$)=N—, —S—C($R^3$)=N—, —O—N=C($R^3$)— and —S—N=C($R^3$)—, wherein the left hand atom or atom group corresponds to $Q^1$.

In particular X is C—$R^3$ or N, $Q^2$ is S or O and $Q^1$ is C—$R^4$ or N and $Q^1$ is connected to X via a double bond while $Q^1$ is connected to X via a single bond.

A particular group of embodiments relates to compounds of the formula I, where X is C—$R^3$ or N, $Q^2$ is S or O and $Q^1$ is C—$R^4$ or N and $Q^1$ is connected to X via a double bond while $Q^2$ is connected to X via a single bond and one of X and $Q^1$ is N, i.e. the moiety -$Q^1$-X-$Q^2$- forms a chain of the following formulae: —N=C($R^3$)—O—, —N=C($R^3$)—S—, —C($R^4$)=N—O— or —C($R^4$)=N—S—, wherein the left hand atom or atom group corresponds to $Q^1$.

A particular group 1 of embodiments relates to compounds of the formula I, where $Q^1$ is N and X is C—$R^3$.

Another particular group 2 of embodiments relates to compounds of the formula I, where $Q^2$ is N and X is C—$R^3$.

A further particular group 3 of embodiments relates to compounds of the formula I, where $Q^1$ is C—$R^4$ and X is N.

A further particular group 4 of embodiments relates to compounds of the formula I, where $Q^2$ is C—$R^4$ and X is N.

A special group 1a of embodiments relates to compounds of the formula I, where $Q^1$ is N, $Q^2$ is O and X is C—$R^3$.

Another special group 2a of embodiments relates to compounds of the formula I, where $Q^2$ is N, $Q^1$ is O and X is C—$R^3$.

A further special group 3a of embodiments relates to compounds of the formula I, where $Q^1$ is C—$R^4$, $Q^2$ is S and X is N.

A further special group 4a of embodiments relates to compounds of the formula I, where $Q^2$ is C—$R^4$, $Q^2$ is S and X is N.

A further special group 1b of embodiments relates to compounds of the formula I, where $Q^1$ is N, $Q^2$ is O and X is C—$R^3$.

A further special group 2b of embodiments relates to compounds of the formula I, where $Q^2$ is N, $Q^1$ is O and X is C—$R^3$.

A further special group 3b of embodiments relates to compounds of the formula I, where $Q^1$ is N, $Q^2$ is S and X is C—$R^3$.

A further special group 4b of embodiments relates to compounds of the formula I, where $Q^2$ is N, $Q^1$ is S and X is C—$R^3$.

Particular groups of embodiments relate to compounds of the formula I, where Y is C—$R^5$.

Other particular groups of embodiments relate to compounds of the formula I, where Y is N.

A particular group 1.1 of embodiments relates to compounds of the formula I, where $Q^1$ is N, X is C—$R^3$ and Y is C—$R^5$.

Another particular group 1.2 of embodiments relates to compounds of the formula I, where $Q^1$ is N, X is C—$R^3$ and Y is N.

A particular group 2.1 of embodiments relates to compounds of the formula I, where $Q^2$ is N, X is C—$R^3$ and Y is C—$R^5$.

A particular group 2.2 of embodiments relates to compounds of the formula I, where $Q^2$ is N, X is C—$R^3$ and Y is N.

A further particular group 3.1 of embodiments relates to compounds of the formula I, where $Q^1$ is C—$R^4$, X is N and Y is C—$R^5$.

Another particular group 3.2 of embodiments relates to compounds of the formula I, where $Q^1$ is C—$R^4$, X is N and Y is N.

A further particular group 4.1 of embodiments relates to compounds of the formula I, where $Q^2$ is C—$R^4$, X is N and Y is C—$R^5$.

A further particular group 4.2 of embodiments relates to compounds of the formula I, where $Q^2$ is C—$R^4$, X is N and Y is N.

A special group 1a.1 of embodiments relates to compounds of the formula I, where $Q^1$ is N, $Q^2$ is O, X is C—$R^3$ and Y is C—$R^5$.

Another special group 1a.2 of embodiments relates to compounds of the formula I, where $Q^1$ is N, $Q^2$ is O, X is C—$R^3$ and Y is N.

Another special group 2a.1 of embodiments relates to compounds of the formula I, where $Q^2$ is N, $Q^1$ is O, X is C—$R^3$ and Y is C—$R^5$.

Another special group 2a.2 of embodiments relates to compounds of the formula I, where $Q^2$ is N, $Q^1$ is O, X is C—$R^3$ and Y is N.

A further special group 3a.1 of embodiments relates to compounds of the formula I, where $Q^1$ is C—$R^4$, $Q^2$ is S, X is N and Y is C—$R^5$.

A further special group 3a.2 of embodiments relates to compounds of the formula I, where $Q^1$ is C—$R^4$, $Q^2$ is S, X is N and Y is N.

A further special group 4a.1 of embodiments relates to compounds of the formula I, where $Q^2$ is C—$R^4$, $Q^2$ is S, X is N and Y is C—$R^5$.

A further special group 4a.2 of embodiments relates to compounds of the formula I, where $Q^2$ is C—$R^4$, $Q^2$ is S, X is N and Y is N.

A further special group 1b.1 of embodiments relates to compounds of the formula I, where $Q^1$ is N, $Q^2$ is O, X is C—$R^3$ and Y is C—$R^5$.

A further special group 1b.2 of embodiments relates to compounds of the formula I, where $Q^1$ is N, $Q^2$ is O, X is C—$R^3$ and Y is N.

A further special group 2b.1 of embodiments relates to compounds of the formula I, where $Q^2$ is N, $Q^1$ is O, X is C—$R^3$ and Y is C—$R^5$.

A further special group 2b.2 of embodiments relates to compounds of the formula I, where $Q^2$ is N, $Q^1$ is O, X is C—$R^3$ and Y is N.

A further special group 3b.1 of embodiments relates to compounds of the formula I, where $Q^1$ is N, $Q^2$ is S, X is C—$R^3$ and Y is C—$R^5$.

A further special group 3b.2 of embodiments relates to compounds of the formula I, where $Q^1$ is N, $Q^2$ is S, X is $C—R^3$ and Y is N.

A further special group 4b.1 of embodiments relates to compounds of the formula I, where $Q^2$ is N, $Q^1$ is S, X is $C—R^3$ and Y is $C—R^5$.

A further special group 4b.2 of embodiments relates to compounds of the formula I, where $Q^2$ is N, $Q^1$ is S, X is $C—R^3$ and Y is N.

Amongst the particular and special groups of embodiments, particular preference is given to embodiments, where $Q^1$ is N and X is $C—R^3$.

Amongst the particular and special groups of embodiments, particular preference is given to embodiments, where $Q^1$ is $C—R^4$ and X is N.

A very special embodiment of the compounds of the invention are those of the following formula I-A, the N-oxides, tautomers, the prodrugs and the pharmaceutically acceptable salts thereof,

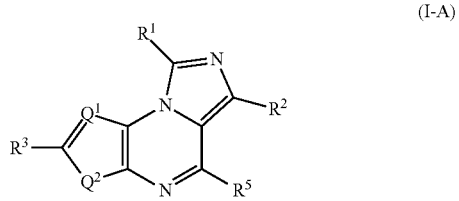

(I-A)

where $Q^2$, $R^1$, $R^2$, $R^3$ and $R^5$ are as defined herein.

Another very special embodiment of the compounds of the invention are those of the following formula I-B, the N-oxides, tautomers, the prodrugs and the pharmaceutically acceptable salts thereof,

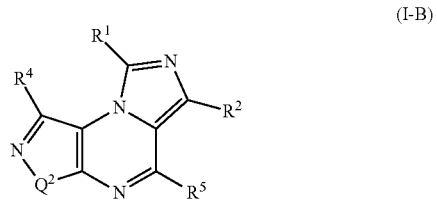

(I-B)

where $Q^2$, $R^1$, $R^2$, $R^4$ and $R^5$ are as defined herein.

Another very special embodiment of the compounds of the invention are those of the following formula I-C, the N-oxides, tautomers, the prodrugs and the pharmaceutically acceptable salts thereof,

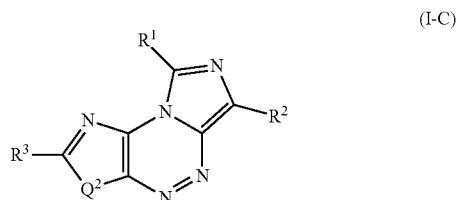

(I-C)

where $Q^2$, $R^1$, $R^2$ and $R^3$ are as defined herein.

Another very special embodiment of the compounds of the invention are those of the following formula I-D, the N-oxides, tautomers, the prodrugs and the pharmaceutically acceptable salts thereof,

(I-D)

where $Q^2$, $R^1$, $R^2$ and $R^4$ are as defined herein.

Preferably, $R^1$ in formulae I, I-A, I-B, I-C and I-D is different from hydrogen. In a particular group of embodiments, the variable $R^1$ in formulae I, I-A, I-B, I-C and I-D is a radical $R^{11}$ or a moiety $Z^1—Ar^1$, where $R^{11}$, $Z^1$ and $Ar^1$ are as defined above.

In this particular group of embodiments, the variable $R^{11}$, is in particular selected from the group consisting of tri-$C_1$-$C_4$-alkylsilyl, $C_1$-$C_8$-alkyl, $C_3$-$C_8$-cycloalkyl and $C_3$-$C_8$-cycloalkyl-$C_1$-$C_4$-alkyl, where the 3 aforementioned substituents may be unsubstituted, partially or completely fluorinated or carry 1, 2 or 3 radicals $R^y$, and C-bound 5- to 8-membered heterocyclyl, which is saturated and has 1 or 2 heteroatom moieties as ring members, which are selected from the group consisting of O, S, $SO_2$ and N—$R^x$, where heterocyclyl is unsubstituted or carries 1, 2, 3 or 4 radicals $R^{yy}$.

In this context, $R^y$ is in particular selected from the group consisting of OH, CN, $C_1$-$C_4$-alkoxy, especially methoxy, and $C_1$-$C_4$-hydroxyalkoxy, especially 2-hydroxyethoxy. In this context, $R^x$ is in particular selected from the group consisting of hydrogen and $C_1$-$C_4$-alkyl, especially methyl.

In this context, $R^{yy}$ is in particular selected from the group consisting of halogen, especially fluorine, $C_1$-$C_4$-alkyl, especially methyl, $C_1$-$C_4$-alkoxy, especially methoxy, $C_1$-$C_2$-fluoroalkyl such as difluoromethyl or trifluoromethyl, and $C_1$-$C_2$-fluoroalkoxy such as difluoromethoxy or trifluoromethoxy.

In this particular group of embodiments, the variable $R^{11}$ is especially selected from the group consisting of $C_1$-$C_8$-alkyl, $C_3$-$C_8$-cycloalkyl, such as cyclopropyl, cyclobutyl, cyclopentyl and cyclohexyl and $C_3$-$C_8$-cycloalkyl-$C_1$-$C_4$-alkyl such as cyclopropylmethyl, cyclobutylmethyl and cyclopentylmethyl and cyclohexyl, where the cycloalkyl moieties in the aforementioned radicals are unsubstituted or carry 1, 2 or 3 radicals selected from fluorine and methyl.

In this particular group of embodiments, the variable $Z^1$, is in particular selected from a single bond, O, $CH_2$, $CH_2CH_2$, $CH_2O$ and $OCH_2$, especially $Z^1$ is a single bond.

In this particular group of embodiments, the variable $Ar^1$, is in particular selected from phenyl and 5- or 6-membered hetaryl having one heteroatom as ring member, which is selected from O, S and N, and optionally one further nitrogen atom as ring member, where phenyl and 5- or 6-membered hetaryl are unsubstituted or carry 1, 2, 3 or 4 identical or different substituents $R^{Ar}$. In this particular group of embodiments, the variable $Ar^1$, is in especially selected from the group consisting of phenyl, thienyl, pyrazolyl, isoxazolyl, thialzolyl and pyridyl, where phenyl, thienyl, pyrazolyl, isoxazolyl, thialzolyl and pyridyl are unsubstituted or carry 1, 2, 3 or 4 identical or different substituents $R^{Ar}$.

In a special group of embodiments, the variable $R^1$ in formulae I, I-A, I-B, I-C and I-D is a radical $Ar^1$, i.e. $Z^1$ is a single bond. In this special group of embodiments, $Ar^1$ is in particular selected from phenyl and 5- or 6-membered hetaryl having one heteroatom as ring member, which is selected from O, S and N, and optionally one further nitrogen atom as ring member, where phenyl and 5- or 6-membered hetaryl are unsubstituted or carry 1, 2, 3 or 4 identical or different substituents R. In this special group of embodiments, the variable $Ar^1$, is in especially selected from the group consisting of phenyl, thienyl, pyrazolyl, isoxazolyl, thialzolyl, 1,2,4-oxadiazolyl and pyridyl, where phenyl, thienyl, pyrazolyl, isoxazolyl, thialzolyl, 1,2,4-oxadiazolyl and pyridyl are unsubstituted or carry 1, 2, 3 or 4 identical or different substituents $R^{Ar}$.

In this context, $R^{Ar}$ is preferably selected from the group consisting of halogen, $C_1$-$C_4$-alkyl, $C_1$-$C_4$-haloalkyl, OH, SH, CN, $CF_3$, O—$CF_3$, COOH, O—$CH_2$—COOH, $C_1$-$C_6$-alkoxy, $C_1$-$C_4$-haloalkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—$(C_1$-$C_6$-alkyl$)_2$, $SO_2N$—$(C_1$-$C_6$-alkyl$)_2$, NH—$SO_2$—$C_1$-$C_4$-alkyl, NH—$SO_2$—$C_1$-$C_4$-haloalkyl, NH—CO—$C_1$-$C_4$-alkyl, NH—CO—$C_1$-$C_4$-haloalkyl, $SO_2$—$C_1$-$C_4$-alkyl, $SO_2$—$C_1$-$C_6$-haloalkyl, phenyl, O-phenyl, O—$CH_2$-phenyl, CONH-phenyl, $SO_2NH$-phenyl, $SO_2$-phenyl, NH—$SO_2$-phenyl, NH—CO-phenyl, CONH-hetaryl, $SO_2NH$-hetaryl, NH—$SO_2$-hetaryl and NH—CO-hetaryl, where hetaryl in the for last mentioned radicals is 5- or 6-membered hetaryl having one heteroatom selected from O, S and N as ring member and optionally one further nitrogen atom as ring member, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy. In this context, $R^{Ar}$ is preferably selected from the group consisting of halogen, especially fluorine or chlorine, $C_1$-$C_4$-alkyl, especially methyl, $C_1$-$C_4$-alkoxy, especially methoxy, $C_1$-$C_2$-fluoroalkyl such as difluoromethyl or trifluoromethyl, and $C_1$-$C_2$-fluoroalkoxy such as difluoromethoxy or trifluoromethoxy.

In another particular group of embodiments, the variable $R^1$ in formulae I, I-A, I-B, I-C and I-D is CN or a moiety $Y^1$—$NR^{17}R^{18}$, where $R^{17}$, $R^{18}$ and $Y^1$ are as defined herein. In particular $Y^1$ is C=O.

Preferably, $R^2$ in formulae I, I-A, I-B, I-C and I-D is different from hydrogen. In a particular group of embodiments, the variable $R^2$ in formulae I, I-A, I-B, I-C and I-D is a radical $R^{21}$ where $R^{21}$ is as defined above. In particular, $R^2$ (and likewise $R^{21}$) is selected from the group consisting of trimethylsilyl, $C_1$-$C_8$-alkyl, $C_3$-$C_8$-cycloalkyl and $C_3$-$C_8$-cycloalkyl-$C_1$-$C_4$-alkyl, where the three last mentioned radicals may be unsubstituted, partially or completely halogenated or where the $C_3$-$C_8$-cycloalkyl radicals may carry 1, 2 or 3 radicals $R^{y'}$, where $R^{y'}$ has one of the meanings given for $R^{y}$, and where $R^{y'}$ is in particular selected from the group consisting of halogen, especially fluorine, $C_1$-$C_4$-alkyl, especially methyl, $C_1$-$C_4$-alkoxy, especially methoxy, $C_1$-$C_2$-fluoroalkyl, especially difluoromethyl or trifluoromethyl, $C_1$-$C_2$-fluoroalkoxy, especially difluoromethoxy or trifluoromethoxy, and where $R^{y'}$ is especially methyl. In this particular group of embodiments $R^2$ is more particularly $C_1$-$C_4$-alkyl, such as methyl or ethyl, $C_1$-$C_2$-alkoxy-$C_1$-$C_2$-alkyl such as methoxymethyl, $C_1$-$C_2$-alkylamino-$C_1$-$C_2$-alkyl, such as methylaminomethyl, or $C_1$-$C_2$-fluoroalkyl, especially difluoromethyl or trifluoromethyl. $R^2$ is especially methyl.

In one embodiment, $R^2$ in formulae I, I-A, I-B, I-C and I-D is different from a group $Z^2$—$Ar^2$.

In another embodiment, $R^2$ in formulae I, I-A, I-B, I-C and I-D is a group $Z^2$—$Ar^2$. In this embodiment $Z^2$ is in particular a single bond. In this special group of embodiments, $Ar^2$ is in particular selected from phenyl and 5- or 6-membered hetaryl having one heteroatom as ring member, which is selected from O, S and N, and optionally one further nitrogen atom as ring member, where phenyl and 5- or 6-membered hetaryl are unsubstituted or carry 1, 2, 3 or 4 identical or different substituents $R^{Ar}$. In this special group of embodiments, the variable $Ar^2$, is in especially selected from the group consisting of phenyl, thienyl, pyrazolyl, isoxazolyl, thialzolyl and pyridyl, where phenyl, thienyl, pyrazolyl, isoxazolyl, thialzolyl and pyridyl are unsubstituted or carry 1, 2, 3 or 4 identical or different substituents $R^{Ar}$. As regards preferred meanings of $R^{Ar}$, reference is made to the preferred and particular meanings of $R^{Ar}$ given above in context with $Ar^1$.

In the compounds of formulae I, where X is C—$R^3$ as well as in the compounds of formulae I-A and I-C, the variable $R^3$ is in particular hydrogen, halogen, especially fluorine, or a radical $OR^{32}$, where $R^{32}$ is as defined above, and where $R^{32}$ is in particular $C_1$-$C_4$-alkyl, such as methyl, or $C_1$-$C_4$-haloalkyl, especially $C_1$-$C_2$-fluoroalkyl, such as difluoromethyl, trifluoromethyl, 2,2-difluoroethyl or 2,2,2-trifluoroethyl.

In particular, $R^3$ is selected from the group consisting of hydrogen, halogen, especially fluorine and $OR^{32}$, where $R^{32}$ is as defined above. $R^3$ is in particular hydrogen, $C_1$-$C_4$-alkoxy or $C_1$-$C_4$-haloalkoxy. $R^3$ is especially hydrogen, $C_1$-$C_4$-alkoxy or $C_1$-$C_2$-fluoroalkoxy and more especially $R^3$ is hydrogen, methoxy, difluoromethoxy, trifluoromethoxy, 2,2-difluoroethoxy or 2,2,2-trifluoroethoxy and most especially $R^3$ is hydrogen.

In the compounds of formulae I, where X is C—$R^3$ as well as in the compounds of formulae I-A and I-C, the variable $R^3$ may also be a group $Z^3$—$Ar^3$.

If $R^4$ is a radical $OR^{42}$ then $R^{42}$ is in particular $C_1$-$C_4$-alkyl, such as methyl, or $C_1$-$C_4$-haloalkyl, especially $C_1$-$C_2$-fluoroalkyl, such as difluoromethyl, trifluoromethyl, 2,2-difluoroethyl or 2,2,2-trifluoroethyl. If $R^3$ is a moiety $Z^3$—$Ar^3$, $Z^3$ is preferably $CH_2$, 1,2-ethandiyl, 1,3-propandiyl, $CH_2O$, $OCH_2$, $CH_2CH_2O$ or $OCH_2CH_2$, wherein 1, 2, 3 or 4 hydrogen atoms may be replaced by a fluorine atom. In these embodiments, $Ar^3$ is in particular selected from the group consisting of C-bound 6-membered monocyclic hetaryl, which has 1 or 2 nitrogen atoms as ring members, and C-bound, 9- or 10-membered, fused bicyclic hetaryl, which has 1 or 2 nitrogen atoms as ring members and optionally a further heteroatom selected from O, S and N as ring member, where monocyclic hetaryl and bicyclic hetaryl may be unsubstituted or may carry 1, 2 or 3 substituents $R^{Ar}$, in particular 0, 1 or 2 substituents $R^{Ar}$. In this regard, $R^{Ar}$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, and fluorinated $C_3$-$C_6$-cycloalkyl. In this regard, $R^{Ar}$ is especially selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

$Ar^3$ is more particularly selected from the group consisting of C-bound, 9- or 10-membered, fused bicyclic hetaryl, which has 1 or 2 nitrogen atoms as ring members and optionally a further heteroatom selected from O, S and N as ring member and which may be unsubstituted or may carry 1, 2 or 3 substituents $R^{Ar}$, in particular 0, 1 or 2 substituents $R^{Ar}$ as defined above. Amongst these, particular preference is given to those compounds, where the $Ar^3$ radical has at least one imino-nitrogen as ring member, which is located in the position adjacent to carbon atom bound to the group $Z^3$. Amongst these, particular preference is given to those, where $Ar^3$ is selected from the group consisting of C-bound, 9- or 10-membered, fused bicyclic hetaryl, which has 1 or 2 nitrogen atoms as ring members and optionally a further heteroatom selected from O, S and N as ring member, where bicyclic hetaryl may be unsubstituted or may carry 1, 2 or 3 substituents $R^{Ar}$, in particular 0, 1 or 2 substituents $R^{Ar}$.

Particular examples of $Ar^3$ are selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^{Ar}$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

In the compounds of formulae I, where $Q^1$ or $Q^2$ is C—$R^4$ as well as in the compounds of formulae I-B and I-D, the variable $R^4$ is in particular selected from the group consisting of halogen, especially fluorine, a radical $OR^{42}$, where $R^{42}$ is as defined above, and a group $Z^4$—$Ar^4$, where $Z^4$ and $Ar^4$ are as defined above.

$R^4$ is in particular selected from the group consisting of hydrogen, halogen, especially fluorine and a radical $OR^{42}$, where $R^{42}$ is as defined above. $R^4$ may also be a group $Z^4$—$Ar^4$, where $Z^4$ and $Ar^4$ are as defined above.

If $R^4$ is a radical $OR^{42}$ then $R^{42}$ is in particular $C_1$-$C_4$-alkyl, such as methyl, or $C_1$-$C_4$-haloalkyl, especially $C_1$-$C_2$-fluoroalkyl, such as difluoromethyl, trifluoromethyl, 2,2-difluoroethyl or 2,2,2-trifluoroethyl.

If $R^4$ is a moiety $Z^4$—$Ar^4$, $Z^4$ is preferably $CH_2$, 1,2-ethandiyl, 1,3-propandiyl, $CH_2O$, $OCH_2$, $CH_2CH_2O$ or $OCH_2CH_2$, wherein 1, 2, 3 or 4 hydrogen atoms may be replaced by a fluorine atom. In these embodiments, $Ar^4$ is in particular selected from the group consisting of C-bound 6-membered monocyclic hetaryl, which has 1 or 2 nitrogen atoms as ring members, and C-bound, 9- or 10-membered, fused bicyclic hetaryl, which has 1 or 2 nitrogen atoms as ring members and optionally a further heteroatom selected from O, S and N as ring member, where monocyclic hetaryl and bicyclic hetaryl may be unsubstituted or may carry 1, 2 or 3 substituents $R^{Ar}$, in particular 0, 1 or 2 substituents $R^{Ar}$. In this regard, $R^{Ar}$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, and fluorinated $C_3$-$C_6$-cycloalkyl. In this regard, $R^{Ar}$ is especially selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

$Ar^4$ is more particularly selected from the group consisting of C-bound, 9- or 10-membered, fused bicyclic hetaryl, which has 1 or 2 nitrogen atoms as ring members and optionally a further heteroatom selected from O, S and N as ring member and which may be unsubstituted or may carry 1, 2 or 3 substituents $R^{Ar}$, in particular 0, 1 or 2 substituents $R^{Ar}$ as defined above. Amongst these, particular preference is given to those compounds, where the $Ar^4$ radical has at least one imino-nitrogen as ring member, which is located in the position adjacent to carbon atom bound to the group $Z^4$. Amongst these, particular preference is given to those, where $Ar^4$ is selected from the group consisting of C-bound, 9- or 10-membered, fused bicyclic hetaryl, which has 1 or 2 nitrogen atoms as ring members and optionally a further heteroatom selected from O, S and N as ring member, where bicyclic hetaryl may be unsubstituted or may carry 1, 2 or 3 substituents $R^{Ar}$, in particular 0, 1 or 2 substituents $R^{Ar}$.

Particular examples of $Ar^4$ are selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^{Ar}$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

If $Q^1$ is C—$R^4$, $R^4$ is in particular hydrogen, fluorine, chlorine, $C_1$-$C_4$-alkoxy or $C_1$-$C_4$-haloalkoxy and especially hydrogen, fluorine, chlorine, methoxy, fluoromethoxy, difluoromethoxy, trifluoromethoxy 2,2-difluoroethoxy or 2,2,2-trifluoroethoxy and more especially hydrogen.

If $Q^2$ is C—$R^4$, $R^4$ is in particular hydrogen, fluorine, chlorine, $C_1$-$C_4$-alkoxy or $C_1$-$C_4$-haloalkoxy and especially hydrogen, fluorine, chlorine, methoxy, fluoromethoxy, difluoromethoxy, trifluoromethoxy 2,2-difluoroethoxy or 2,2,2-trifluoroethoxy or a radical $Z^4$—$Ar^4$, where $Z^4$ and $Ar^4$ are as defined above and where $Z^4$ and $Ar^4$ in particular have the particular or special meanings given above.

In the compounds of formulae I, where Y is C—$R^5$ as well as in the compounds of formulae I-A and I-B, a particular group of embodiments relates to compounds of the formulae I, I-A and I-B, where the variable $R^5$ is selected from the group consisting of hydrogen, halogen and a radical $R^{51}$, where $R^{51}$ is as defined above, and wherein $R^{51}$ is particularly selected from the group consisting of $C_1$-$C_4$-alkyl, which is unsubstituted or carries a hydroxyl group, and $C_1$-$C_4$-haloalkyl.

Especially, $R^5$ is methyl, $CH_2F$, $CHF_2$, $CF_3$ or $CH_2OH$

In the compounds of formulae I, where Y is C—$R^5$ as well as in the compounds of formulae I-A and I-B, another particular group of embodiments relates to compounds of the formulae I, I-A and I-B, where the variable $R^5$ is a radical $Y^1$—$NR^{57}R^{58}$, $Y^1$—$N(R^{59})$—$Y^3$—$NR^{57}R^{58}$ or $Y^1$—$N(R^{59})$—$Y^2$—$R^{55a}$.

If $R^5$ is a radical $Y^1$—$NR^{57}R^{58}$, $Y^1$—$N(R^{59})$—$Y^3$—$NR^{57}R^{58}$ or $Y^1$—$N(R^{59})$—$Y^2$—$R^{55a}$, $Y^1$ is in particular a single bond or $CH_2$. $Y^3$ is preferably a bond or C(=O). $Y^2$ is preferably C(=O). $R^{57}$ and $R^{58}$ are in particular, independently of each other $C_1$-$C_4$-alkyl or hydroxyl-$C_2$-$C_4$-alkyl, or $NR^{57}R^{58}$ forms a saturated or aromatic N-bound 5-, 6- or 7-membered heterocyclyl, which in addition to the nitrogen atom may have 1 or 2 further heteroatom moieties as ring members, which are selected from the group consisting of O, N, S, S(O), $S(O)_2$ or N—$R^x$, where heterocyclyl is unsubstituted or carries 1, 2, 3 or 4 $C_1$-$C_4$-alkyl groups and where $R^x$ is hydrogen or methyl. Examples of such cyclic moieties $NR^{57}R^{58}$ are morpholinyl, pyrrolidinyl, piperazinyl, N-methylpiperazinyl, 1H-imidazol-1-yl, 4-methyl-2-ethyl-1H-imidazol-1-yl or 4-methyl-2-ispropyl-1H-imidazol-1-yl. $R^{55a}$ is in particular hydrogen, $C_1$-$C_4$-alkyl or $C_1$-$C_4$-haloalkyl.

$R^5$ may also be a group $Z^5$—$Ar^5$, where $Z^5$ and $Ar^5$ are as defined above.

If $R^5$ is a moiety $Z^5$—$Ar^5$, $Z^5$ is preferably $CH_2$, 1,2-ethandiyl, 1,3-propandiyl, $CH_2O$, $OCH_2$, $CH_2CH_2O$ or $OCH_2CH_2$, wherein 1, 2, 3 or 4 hydrogen atoms may be replaced by a fluorine atom. In these embodiments, $Ar^5$ is in particular selected from the group consisting of C-bound 6-membered monocyclic hetaryl, which has 1 or 2 nitrogen atoms as ring members, and C-bound, 9- or 10-membered, fused bicyclic hetaryl, which has 1 or 2 nitrogen atoms as ring members and optionally a further heteroatom selected from O, S and N as ring member, where monocyclic hetaryl and bicyclic hetaryl may be unsubstituted or may carry 1, 2 or 3 substituents $R^{Ar}$, in particular 0, 1 or 2 substituents $R^{Ar}$. In this regard, $R^{Ar}$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, and fluorinated $C_3$-$C_6$-cycloalkyl. In this regard, $R^{Ar}$ is especially selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

$Ar^5$ is more particularly selected from the group consisting of C-bound, 9- or 10-membered, fused bicyclic hetaryl, which has 1 or 2 nitrogen atoms as ring members and optionally a further heteroatom selected from O, S and N as ring member and which may be unsubstituted or may carry 1, 2 or 3 substituents $R^{Ar}$, in particular 0, 1 or 2 substituents $R^{Ar}$ as defined above. Amongst these, particular preference is given to those compounds, where the $Ar^5$ radical has at least one imino-nitrogen as ring member, which is located in the position adjacent to carbon atom bound to the group $Z^5$. Amongst these, particular preference is given to those, where $Ar^5$ is selected from the group consisting of C-bound, 9- or 10-membered, fused bicyclic hetaryl, which has 1 or 2 nitrogen atoms as ring members and optionally a further heteroatom selected from O, S and N as ring member, where bicyclic hetaryl may be unsubstituted or may carry 1, 2 or 3 substituents $R^{Ar}$, in particular 0, 1 or 2 substituents $R^{Ar}$.

Particular examples of $Ar^5$ are selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^{Ar}$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

In particular embodiments of the invention $R^4$ and $R^5$, together with the carbon atoms, to which they are attached, may also form a fused 5-, 6- or 7-membered saturated heterocyclic ring, where the fused heterocyclic ring has 1 or 2 oxygen atoms as ring members and where the fused heterocyclic ring is unsubstituted or may carry 1 or 2 radicals selected from methyl, methoxy and fluorine. In particular the radicals $R^4$ and $R^5$ together may form a moiety $OCH_2O$ or $OCF_2O$. In these particular embodiments, $R^3$ is preferably hydrogen.

$R^5$ is in particular hydrogen, fluorine, $C_1$-$C_4$-alkoxy or $C_1$-$C_4$-haloalkoxy and especially fluorine, chlorine, methoxy, fluoromethoxy, difluoromethoxy, trifluoromethoxy, 2,2-difluoroethoxy or 2,2,2-trifluoroethoxy.

In the aforementioned particularly preferred embodiments Y is preferably CH or C—$CH_3$.

Apart from that, the variables $R^{Ar}$, $Y^1$, $Y^2$, $Y^3$, $Y^4$, $Y^5$, $Y^6$, $R^x$, $R^y$, $R^{yy}$, $R^{y1}$, $R^{y1}$, $R^{y2}$, $R^{y3}$, $R^{y4}$, $R^{y5}$, $R^{y6}$, $R^{y7}$, $R^{y8}$, $R^{y9}$, $R^{y0}$, $R^z$, $R^{Ar1}$, $R^{Ar2}$, $R^{Ar3}$, $R^{Ar4}$, $R^{Ar5}$, $R^{Ar6}$, $R^{Ar7}$, $R^{Ar8}$, $R^{Ar9}$, $R^{Ar0}$, $R^{12}$, $R^{13}$, $R^{14}$, $R^{15}$, $R^{15a}$, $R^{16}$, $R^{17}$, $R^{18}$, $R^{19}$, $R^{22}$, $R^{23}$, $R^{24}$, $R^{25}$, $R^{26}$, $R^{27}$, $R^{28}$, $R^{31}$, $R^{33}$, $R^{34}$, $R^{35}$, $R^{35a}$, $R^{36}$, $R^{37}$, $R^{38}$, $R^{39}$, $R^{41}$, $R^{43}$, $R^{44}$, $R^{45}$, $R^{45a}$, $R^{46}$, $R^{47}$, $R^{48}$, $R^{49}$, $R^{51}$, $R^{53}$, $R^{54}$, $R^{55}$, $R^{55a}$ and $R^{56}$ particularly have, irrespectively of their occurrence and with regard to the formulae I, I-A, I-B, I-C and I-D and with regard to each of the above mentioned embodiments, groups of embodiments and particularly preferred embodiments one of the following meanings:

$Y^1$ is in particular a single bond, $CH_2$, $CH_2CH_2$, $OCH_2$, $OCH_2CH_2$, $C(\!=\!O)$, $OC(\!=\!O)$, $CH_2C(\!=\!O)$.

$Y^2$ is in particular a single bond, O, $CH_2O$, $CH_2CH_2O$, $C(\!=\!O)$, $C(\!=\!O)O$, $CH_2C(\!=\!O)$, $CH_2C(\!=\!O)O$ or $SO_2$.

$Y^3$ is in particular a single bond, $CH_2$, $CH_2CH_2$ or $C(\!=\!O)$.

$Y^5$, $Y^6$, independently of each other, are in particular a single bond, $CH_2$ or $CH_2CH_2$.

$R^{31}$, $R^{41}$, $R^{51}$, $R^{y1}$, $R^{Ar1}$, independently of each other, are in particular trimethylsilyl, $C_1$-$C_4$-alkyl, $C_1$-$C_4$-haloalkyl, $C_3$-$C_6$-cycloalkyl, $C_3$-$C_6$-cycloalkylmethyl or $C_3$-$C_4$-alkenyl, especially methyl, ethyl, difluoromethyl, trifluoromethyl, cyclopropyl, cyclobutyl or cyclopropylmethyl, more especially methyl, difluoromethyl or trifluoromethyl.

$R^{12}$, $R^{22}$, $R^{y2}$, $R^{Ar2}$, independently of each other, are in particular trimethylsilyl, $C_1$-$C_4$-alkyl, $C_1$-$C_4$-haloalkyl, $C_3$-$C_6$-cycloalkyl, $C_3$-$C_6$-cycloalkylmethyl or $C_3$-$C_4$-alkenyl, especially methyl, ethyl, difluoromethyl, trifluoromethyl, cyclopropyl, cyclobutyl or cyclopropylmethyl.

$R^{13}$, $R^{33}$, $R^{43}$, $R^{53}$, $R^{y3}$, $R^{Ar3}$, independently of each other, are in particular $C_1$-$C_4$-alkyl or $C_1$-$C_4$-haloalkyl, especially methyl, ethyl, difluoromethyl or trifluoromethyl.

$R^{14}$, $R^{23}$, $R^{34}$, $R^{44}$, $R^{54}$, $R^{y4}$, $R^{Ar4}$, independently of each other, are in particular $C_1$-$C_4$-alkyl, $C_1$-$C_4$-haloalkyl, $C_3$-$C_6$-cycloalkyl or $C_3$-$C_6$-cycloalkylmethyl, especially methyl, ethyl, difluoromethyl, trifluoromethyl, cyclopropyl, cyclobutyl or cyclopropylmethyl;

$R^{15}$, $R^{24}$, $R^{35}$, $R^{45}$, $R^{55}$, $R^{y5}$, $R^{Ar5}$, independently of each other, are in particular $C_1$-$C_4$-alkyl, $C_3$-$C_6$-cycloalkyl or $C_3$-$C_6$-cycloalkylmethyl, especially methyl, ethyl, cyclopropyl, cyclobutyl or cyclopropylmethyl.

$R^{16}$, $R^{36}$, $R^{46}$, $R^{56}$, $R^{y6}$, $R^{Ar6}$, independently of each other, are in particular $C_1$-$C_4$-alkyl, $C_1$-$C_4$-haloalkyl, $C_3$-$C_6$-cycloalkyl or $C_3$-$C_6$-cycloalkylmethyl, especially methyl, ethyl, difluoromethyl, trifluoromethyl, cyclopropyl, cyclobutyl or cyclopropylmethyl.

$R^{17}$, $R^{25}$, $R^{37}$, $R^{47}$, $R^{57}$, $R^{y7}$, $R^{Ar7}$, independently of each other, are in particular hydrogen, $C_1$-$C_4$-alkyl or $C_3$-$C_4$-alkenyl, especially hydrogen, methyl, ethyl, propyl, isopropyl or 2-propenyl.

$R^{18}$, $R^{26}$, $R^{48}$, $R^{58}$, $R^{y8}$, $R^{Ar8}$, independently of each other, are in particular hydrogen, $C_1$-$C_4$-alkyl or $C_3$-$C_4$-alkenyl, especially hydrogen, methyl, ethyl, propyl, isopropyl or 2-propenyl.

$R^{17}$ and $R^{18}$, $R^{25}$ and $R^{26}$, $R^{37}$ and $R^{38}$, $R^{47}$ and $R^{48}$, $R^{57}$ and $R^{58}$, $R^{y7}$ and $R^{y8}$, or $R^{Ar7}$ and $R^{Ar8}$, respectively, together with the nitrogen atom to which they are bound may also form a saturated N-bound heterocyclic radical, selected from the group consisting of pyrrolidin-1-yl, piperidin-1-yl, morpholin-4-yl, thiomorpholin-4-yl, piperazin-1-yl and 4-methylpiperazin-1-yl, where the 6 aforementioned heterocyclic radicals may carry 1, 2, 3 or 4 substituents, selected from methyl and fluorine.

$R^{19}$, $R^{27}$, $R^{39}$, $R^{49}$, $R^{59}$, $R^{y9}$, $R^{Ar9}$, $R^z$, independently of each other, are in particular hydrogen, $C_1$-$C_4$-alkyl or $C_3$-$C_4$-alkenyl, especially hydrogen, methyl, ethyl, propyl, isopropyl or 2-propenyl;

$R^{15a}$, $R^{25a}$, $R^{35a}$, $R^{45a}$, $R^{55a}$, $R^{y0}$, $R^{Ar0}$, independently of each other, are in particular trimethylsilyl, $C_1$-$C_4$-alkyl, $C_1$-$C_4$-haloalkyl, $C_3$-$C_6$-cycloalkyl, $C_3$-$C_6$-cycloalkylmethyl or $C_3$-$C_4$-alkenyl, especially methyl, ethyl, difluoromethyl, trifluoromethyl, cyclopropyl, cyclobutyl or cyclopropylmethyl, more especially methyl, difluoromethyl or trifluoromethyl.

$R^y$ is in particular selected from the group consisting of OH, CN, $C_1$-$C_4$-alkoxy, especially methoxy, and $C_1$-$C_4$-hydroxyalkoxy, especially 2-hydroxyethoxy.

$R^x$ is in particular selected from the group consisting of hydrogen and $C_1$-$C_4$-alkyl, especially methyl.

$R^{yy}$ is in particular selected from the group consisting of halogen, especially fluorine, $C_1$-$C_4$-alkyl, especially methyl, $C_1$-$C_4$-alkoxy, especially methoxy, $C_1$-$C_2$-fluoroalkyl such as difluoromethyl or trifluoromethyl, and $C_1$-$C_2$-fluoroalkoxy such as difluoromethoxy or trifluoromethoxy.

Particular embodiments of the invention relates to the compounds of formula I, to the N-oxides, the prodrugs, the hydrates and the tautomers thereof and to the pharmaceutically suitable salts thereof, where the compounds of the formula I are selected from the group consisting of:

5,6-dimethyl-8-(3-nitrophenyl)-3-thia-1,4,7,8a-tetraaza-as-indacene,
5,6-dimethyl-8-(2-methylpyridin-3-yl)-3-thia-1,4,7,8a-tetraaza-as-indacene,
5,6-dimethyl-8-propyl-3-thia-1,4,7,8a-tetraaza-as-indacene,
5,6-dimethyl-8-(3-methylpyridin-4-yl)-3-thia-1,4,7,8a-tetraaza-as-indacene,
5,6-dimethyl-8-(6-methylpyridin-3-yl)-3-thia-1,4,7,8a-tetraaza-as-indacene,
5,6-dimethyl-8-bromo-3-thia-1,4,7,8a-tetraaza-as-indacene,
5,6-dimethyl-3-thia-1,4,7,8a-tetraaza-as-indacene,
2,5,6-trimethyl-8-propyl-3-thia-1,4,7,8a-tetraaza-as-indacene,
2-methoxy-5,6-dimethyl-8-propyl-3-thia-1,4,7,8a-tetraaza-as-indacene,
5,6-Dimethyl-8-propyl-1-thia-3,4,7,8a-tetraaza-as-indacene,
3-(5,6-Dimethyl-3-thia-1,4,7,8a-tetraaza-as-indacen-8-yl)-benzamide and
5,6-Dimethyl-8-(2-methyl-pyridin-4-yl)-3-thia-1,4,7,8a-tetraaza-as-indacene.

The compounds of the invention of the general formulae I, I-A, I-B, I-C and I-D and the starting materials used to prepare them can be prepared in analogy to known processes of organic chemistry as are described in standard works of organic chemistry, e.g. Houben-Weyl, "Methoden der Organischen Chemie", Thieme-Verlag, Stuttgart, Jerry March "Advanced Organic Chemistry", 5$^{th}$ edition, Wiley & Sons and the literature cited therein, and R. Larock, "Comprehensive Organic Transformations", 2$^{nd}$ edition, Weinheim, 1999 and the literature cited therein. The compounds of the invention of the general formula I are advantageously prepared by the methods described below and/or in the experimental section.

Compounds of the formula I, wherein Y is C—$R^3$ can be prepared e.g. by reacting a compound of the formula II with a cyclizing agent as depicted in scheme 1.

Scheme 1:

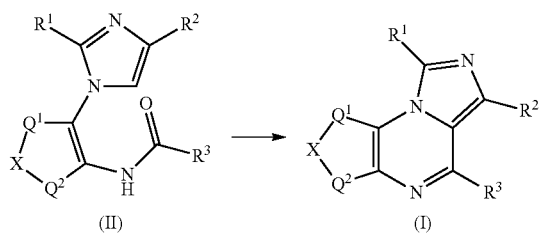

In Scheme 1, $R^1$, $R^2$, $R^3$, X, $Q^1$ and $Q^2$ are as defined above. The cyclisation can be performed by analogy to known cyclization reactions (see e.g. US 2009143361). Suitable cyclizing agents are, for example, phosphoryl chloride ($POCl_3$), phosphorus pentachloride, pentoxide, phosphorus pentoxide or thionyl chloride. It may be advantageous to use a combination of two cyclizing agents such as $P_2O_5$/$POCl_3$.

The compounds of formula I, where Y is N, may be prepared by intramolecular cyclization of a diazonium compound, which is prepared from the corresponding 5-amino-4-hetarylimidazole compound of formula III as depicted in scheme 2:

Scheme 2:

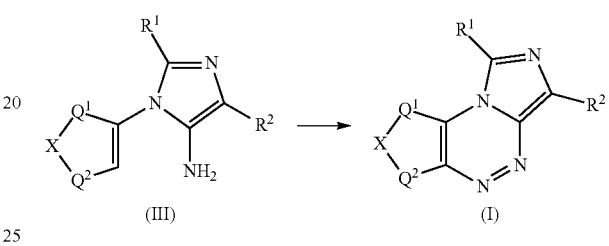

In Scheme 2, $R^1$, $R^2$, X, $Q^1$ and $Q^2$ are as defined above. The intramolecular cyclization of the compound of formula III, via its diazonium compound to the compound I can be performed by analogy to known intramolecular cyclization reactions. Typical reaction conditions are those described by C. L. Bogza et al. in Chemistry of Heterocyclic Compounds, Vol. 40, (2004), 1506.

Compounds of the formula I, wherein $R^1$ is selected from a C-bound radicals, such as $Z^1$—$Ar^1$ with $Z^1$ being a single bond or $C_1$-$C_4$-alkylene or $R^{11}$, can be prepared e.g. by reacting a compound of the formula I'', wherein $R^1$ is a suitable leaving group Lg, such as chlorine, bromine or iodine, triflate or nonaflate, with a compound M-$R^1$, as depicted in scheme 3.

Scheme 3:

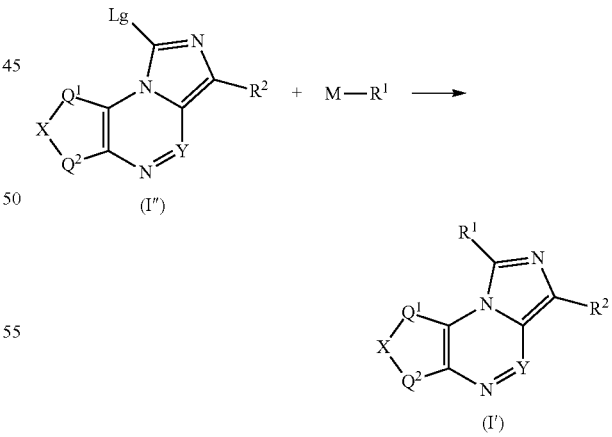

Compound of formula I'' corresponds to compound of formula I, where $R^1$ is a leaving group Lg. Suitable leafing groups Lg in formula I'' include, but are not limited to halogen such as chlorine, bromine or iodine, alkylsulfonate such as methylsulfonate, phenylsulfonate, alkylphenylsulfonate such as tosylate and perfluoroalkylsulfonate such as triflate, pentaflate, heptaflate or nonaflate. In formula M-$R^1$, M relates to a metal or metal bound organometal group, such as Li, MgHal, ZnHal, with Hal being Cl, Br or I, a group $Sn(R^{Sn})_3$ wherein $R^{Sn}$ is $C_1$-$C_6$-alkyl or $C_3$-$C_6$-cycloalkyl or phenyl. M may also be $B(OR^{B1})(OR^{B2})$ radical, where $R^{B1}$ and $R^{B2}$ are, independently of each other, hydrogen or $C_1$-$C_4$-alkyl or $R^{B1}$ and $R^{B2}$ together form a $C_2$-$C_6$-alkanediyl moiety, e.g. ethan-1,2-diyl, propan-1,3-diyl or 1,1,2,2-tetramethylethan-1,2-diyl.

The reaction of the compound M-$R^1$ with the compound I" can be performed by analogy to known coupling reactions in the presence of suitable transition metal catalysts, in particular palladium catalysts. Typical reactions conditions are those of Stille coupling and related reactions (see e.g. Stille et al. Angew. Chem. Int. Ed. Engl. 1986, 25,508; J. Elugeuro et al.; Synthesis 1997, 5, 563-566) or Suzuki coupling (see e.g. A. Suzuki et al, Chem. Rev. 1995, 95, 2457-2483, N. Zhe et al.; J. Med. Chem. 2005, 48 (5), 1569-1609; Young et al.; J. Med. Chem. 2004, 47 (6), 1547-1552; C. Slee et al.; Bioorg. Med. Chem. Lett. 2001, 9, 3243-3253, T. Zhang et al. Tetrahedron Lett., 52 (2011), 311-313, S. Bourrain et al., Synlett. 5 (2004), 795-798).

It is also possible to convert the compound of the formula I, wherein $R^1$ is halogen into the corresponding organometal compound, where $R^1$ is a group M as defined above.

Compounds of the formula I, where $R^1$ is a N-bound radical can be obtained by a coupling reaction between the compound I" and the corresponding amine in the presence of a palladium catalyst in terms of a Buchwald-Hartwig reaction. Suitable palladium catalyst are for example tris-(dibenzylideneacetone)dipalladium(0) ($Pd_2(dba)_3$), [1,1-bis(diphenylphosphino)ferrocene]dichloropalladium(II) ($PdCl_2$(dppf)) or palladium acetate ($Pd(OAc)_2$). The reaction is usually carried out in the presence of a tri(substituted)phosphine, e.g. a triarylphosphine such as triphenylphosphine, tritolylphosphine or 2,2'-bis(diphenylphosphino)-1,1'-binaphthalene (BINAP), tri(cyclo)alkylphosphine such as tris-n-butylphosphine, tris(tert-butyl)phosphine or tris(cyclohexylphosphine), or dicyclohexyl-(2',4',6'-tri-iso-propyl-biphenyl-2-yl)-phosphane (X-Phos). Usually, the reaction is performed in the presence of a base such as an alkaline alkoxide, earth alkine alkoxide, alkaline carbonate or earth alkaline carbonate such as or sodium tert-butoxide or cesium carbonate.

Compounds of the formula I, where $R^1$ is a O-bound radical or an S-bound radical can be obtained by a coupling reaction between the compound I" and the corresponding alcohol or mercaptan in the presence of a strong base.

Compounds of the formula I, where $R^1$ is a $C(O)OR^{14}$ radical can be prepared by esterification of the corresponding acid, where $R^1$ is C(O)OH.

Compounds of the formula I, where $R^1$ is a $OC(O)R^{16}$ radical can be prepared from the corresponding OH compound, where $R^1$ is OH, by an esterification.

Compounds of the formula I, where $R^1$ halogen, in particular chlorine, bromine or iodine, can be prepared from the corresponding OH compound, where $R^1$ is OH.

Compounds of the formula I, where $R^1$ halogen, in particular chlorine or bromine, can also be prepared by selective halogenation of the corresponding unsubstituted compound, where $R^1$ is hydrogen.

Compounds of the formula II may be prepared by reacting a halogenohetaryl compound of the formula IV with a suitable imidazole compound V in the presence of a catalyst in terms of a modified Ullmann reaction as depicted in scheme 4.

Scheme 4:

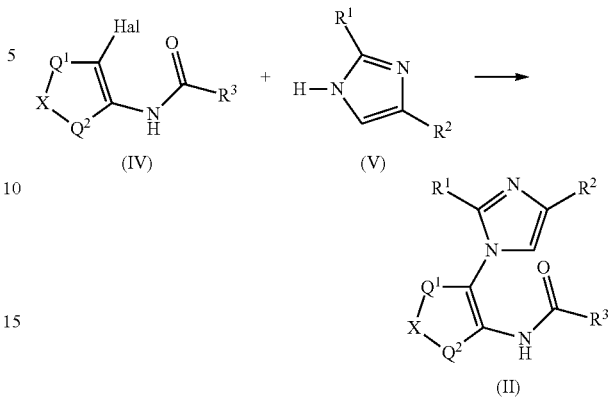

In Scheme 3, $R^1$, $R^2$, $R^3$, X, $Q^1$ and $Q^2$ are as defined above, Hal is halogen, preferably bromine or chlorine. Suitable catalysts are copper(I) compounds, e.g. copper(I) iodide. Advantageously the reaction is also performed in the presence of a diamine ligand. Suitable diamine ligands are 1,10-phenanthroline, trans-N,N'-dimethylcyclohexane-1,2-diamine or trans 1,2-cyclohexanediamine. Usually, the reaction is performed in the presence of a base, such as alkaline carbonates such as cesium carbonate or potassium carbonate.

Compounds of the formula I, where $R^1$ is halogen can be prepared by reacting a compound of the formula I where $R^1$ is hydrogen with a halogenating agent. Suitable brominating agents are bromine, N-bromosuccinimide (NBS) and pyridinium tribromide. A suitable chlorinating agent is N-chlorosuccinimide.

Compounds of the formula I, where $R^3$ is halogen can be prepared by reacting a compound of the formula I where $R^3$ is hydrogen with a halogenating agent. Suitable brominating agents are bromine, N-bromosuccinimide (NBS) and pyridinium tribromide. A suitable chlorinating agent is N-chlorosuccinimide.

Compounds of the formula I, where $R^3$ is $OR^{32}$ can be prepared by substitution reaction from the corresponding halogen compound, where $R^3$ is halogen.

The N-oxides of compound I may be prepared from the compounds of formula I according to conventional oxidation methods, for example by treating said compounds with an organic peracid; such as metachloroperbenzoic acid or 3-chloroperbenzoic acid [Journal of Medicinal Chemistry 38(11), 1892-1903 (1995), WO 03/64572]; or with inorganic oxidizing agents; such as hydrogen peroxide [cf. Journal of Heterocyclic Chemistry 18 (7), 1305-1308 (1981)] or oxone [cf. Journal of the American Chemical Society 123(25), 5962-5973 (2001)]. The oxidation may lead to pure mono-N-oxides or to a mixture of different N-oxides, which can be separated by conventional methods; such as chromatography.

The reactions are usually performed in an organic solvent, including aprotic organic solvent, e.g. substituted amides, lactames and ureas; such as dimethylformamide, dimethylacetamide, N-methylpyrrolidone, tetramethyl urea, cyclic ethers; such as dioxane, tetrahydrofurane, halogenated hydrocarbons; such as dichloromethane, and mixtures thereof as well as mixtures thereof with $C_1$-$C_6$-alkanols and/or water.

The reactions described above will be usually performed at temperatures ranging from $-10°$ C. to $100°$ C., depending on the reactivity of the used compounds.

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

Due to their capability of inhibiting PDE10A at low concentrations, the compounds of the formula I, their N-oxides, their hydrates, their tautomers and their prodrugs and the pharmaceutically acceptable salts thereof, are particularly suitable for treating disorders or conditions, which can be treated by inhibition of phosphodiesterase type 10A. The terms "treating" and "treatment" in terms of the present invention have to be understood to include both curative treatment of the cause of a disease or disorder, the treatment of the symptoms associated with a disease or disorder, i.e. controlling the disease or disorder or ameliorating the conditions or symptoms associated with a disease or disorder, and prophylactic treatment, i.e. a treatment for reducing the risk of a disease or disorder.

Neurological and psychiatric disorders or conditions which can be treated by inhibition of PDE10A, including curative treatment, control or amelioration and prophylaxis, include CNS disorders, in particular schizophrenia, depression, bipolar disorders, cognitive dysfunctions associated with schizophrenia, cognitive dysfunctions associated with Alzheimer's disease, Huntington's disease (Huntington chorea), anxiety and substance-related disorders, especially substance use disorder, substance tolerance conditions associated with substance withdrawal. Disorders or conditions which can be treated by inhibition of PDE10A, including curative treatment, control or amelioration and prophylaxis, also include treatment of diet induced obesity.

Thus, the invention relates to the use of compounds of formula I, their N-oxides, their hydrates, their tautomers and their prodrugs and the pharmaceutically acceptable salts thereof, for treatment of disorders or conditions, which can be treated by inhibition of phosphodiesterase type 10A, i.e. the invention relates to the use of such compounds for curative treatment of such a disease or disorder, controlling such a disease or disorder, ameliorating the symptoms associated with such a disease or disorder and reducing the risk for such a disease or disorder.

The present invention also relates to a method for the treatment of a medical disorder, selected from neurological and psychiatric disorders which can be treated by inhibition of phosphodiesterase type 10A, said method comprising administering an effective amount of at least one compound, selected from the group of compounds of formula I, their N-oxides, their hydrates, their tautomers, their prodrugs and the pharmaceutically acceptable salts thereof, to a mammal in need thereof.

The present invention in particular relates to:

a method for treating, controlling, ameliorating or reducing the risk of schizophrenia in a mammalian;

a method for treating, controlling, ameliorating or reducing the risk of cognitive disturbances associated with schizophrenia in a mammalian;

a method for treating, controlling, ameliorating or reducing the risk of depression in a mammalian;

a method for treating, controlling, ameliorating or reducing the risk of bipolar disorders in a mammalian;

a method for treating, controlling or ameliorating substance (drug) abuse;

a method for treating or ameliorating the symptoms associated with substance use disorders in a mammalian;

a method for treating or ameliorating the symptoms associated with diet-induced obesity in a mammalian;

a method for treating, controlling, ameliorating or reducing the risk of cognitive disturbances associated with Alzheimer's disease in a mammalian;

a method for treating, controlling, ameliorating or reducing the risk of behavioral symptoms in Alzheimer's disease;

a method for treating, controlling, ameliorating or reducing the risk of anxiety in a mammalian;

a method for treating, controlling, ameliorating or reducing the risk of Huntington's disease in a mammalian;

which methods comprising administering an effective amount of at least one compound, selected from the group of compounds of formula I, their N-oxides, their hydrates, their tautomers, their prodrugs and the pharmaceutically acceptable salts thereof, to a mammal in need thereof.

The subject treated in the present methods is generally a mammal, preferably a human being, male or female, in whom inhibition of PDE10A is desired. The terms "effective amount" and "therapeutically effective amount" mean the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes, wherein there may be a slowing, interrupting, arresting, controlling, or stopping of the progression of the disorders described herein, but does not necessarily indicate a total elimination of all disorder symptoms, as well as the prophylactic therapy of the mentioned conditions, particularly in a patient who is predisposed to such disease or disorder. The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

A preferred embodiment of the present invention provides a method for treating schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating cognitive disturbances associated with schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

At present, the fourth edition of the Diagnostic and Statistical Manual of Mental Disorders (DSM-IV) (1994, American Psychiatric Association, Washington, D.C.), provides a diagnostic tool including schizophrenia and other psychotic disorders. These include: disorders having psychotic symptoms as the defining feature. The term psychotic refers to delusions, prominent hallucinations, disorganized speech, disorganized or catatonic behavior. The disorder includes: paranoid, disorganized, catatonic, undifferentiated, and residual schizophrenia, schizophreniform disorder, schizoaffective disorder, delusional disorder, brief psychotic disorder, shared psychotic disorder, psychotic disorder due to a general medical condition, substance-induced psychotic disorder, and psychotic disorder not otherwise specified. The skilled artisan will recognize that there are alternative nomenclatures, nosologies, and classification systems for neurological and psychiatric disorders, and particular schizophrenia, and that these systems evolve with medical scientific progress. Thus, the term "schizophrenia" is intended to include like disorders that are described in other diagnostic sources.

In another preferred embodiment, the present invention provides a method for treating substance-related disorders, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating anxiety, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, posttraumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another preferred embodiment, the present invention provides a method for treating depression, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-1V.

In another preferred embodiment, the present invention provides a method for treating substance-related disorders, especially substance dependence, substance abuse, substance tolerance, and substance withdrawal, comprising: administering to a patient in need thereof an effective amount at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including disorders related to taking a drug of abuse (including alcohol), to the side effects of a medication, and to toxin exposure. Substances include alcohol, amphetamine and similarly acting sympathomimetics, caffeine, cannabis, cocaine, hallucinogens, inhalants, nicotine, opioids, phencyclidine (PCP) or similarly acting arylcyclohexylamines, and sedatives, hypnotics, or anxiolytics. Also, polysubstance dependence and other unknown substance-related disorders are included. The skilled artisan will recognize that there are alternative nomenclatures, nosologies, and classification systems for neurological and psychiatric disorders, and particular substance-related disorders, and that these systems evolve with medical scientific progress. Thus, the term "substance-related disorder" is intended to include like disorders that are described in other diagnostic sources.

In the treatment, prevention, control, amelioration, or reduction of risk of conditions which require inhibition of PDE10A an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. When treating, preventing, controlling, ameliorating, or reducing the risk of neurological and psychiatric disorders or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams, in the case of a 70 kg adult human, the total daily dose will generally be from about 7 milligrams to about 350 milligrams. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention may be administered by conventional routes of administration, including parenteral (e.g., intramuscular, intrapentoneal, intravenous, ICV, intracisternal injection or infusion, subcutaneous injection, or implant), oral, by inhalation spray, nasal, vaginal, rectal, sublingual, or topical routes of administration.

The compounds according to the present invention are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The present invention also relates to pharmaceutical compositions (i.e. medicaments) which comprise at least one compound of the present invention and, where appropriate, one or more suitable excipients.

These excipients/drug carriers are chosen according to the pharmaceutical form and the desired mode of administration.

The compounds of the present invention can be used to manufacture pharmaceutical compositions for parenteral (e.g., intramuscular, intrapentoneal, intravenous, ICV, intracisternal injection or infusion, subcutaneous injection, or implant), oral, sublingual, intratracheal, intranasal, topical, transdermal, vaginal or rectal administration, and be administered to animals or humans in unit dose forms, mixed with conventional pharmaceutical carriers, for the prophylaxis or treatment of the above impairments or diseases.

In the pharmaceutical compositions, the at least one compound of the present invention may be formulated alone or together with further active compounds, in suitable dosage unit formulations containing conventional excipients, which generally are non-toxic and/or pharmaceutically acceptable. Carriers or excipients can be solid, semisolid or liquid materials which serve as vehicles, carriers or medium for the active compound. Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorfi ECV-Editio-Kantor-Verlag, 1996.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their prodrugs, their N-oxides, their tautomers, their hydrates or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

When producing the pharmaceutical compositions, the compounds according to the invention are optionally mixed or diluted with one or more carriers.

The following examples are intended for further illustration of the present invention.

EXAMPLES

Abbreviations:
Ac$_2$O acetic anhydride
AcOH acetic acid
DCM dichloromethane
DMF dimethylformamide
DMSO dimethyl sulfoxide
DPPA diphenylphosphoryl azide
EA ethyl acetate
Et ethyl
hr hour
Pd(dppf)Cl$_2$[1,1'-Bis(diphenylphosphino)ferrocene] dichloropalladium(II)
PE petrol ether
pre-HPLC preparative HPLC
RT retention time
tert-BuOH tert butanol
THF tetrahydrofuran The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m). Coupling constants are in units of hertz (Hz).

Generally, LC-MS was recorded on Agilent 1200 HPLC/6110 SQ system. All mass spectra were taken under electrospray ionisation (ESI) methods.

I. Preparation Examples

Example 1

5,6-Dimethyl-8-propyl-3-thia-1,4,7,8a-tetraaza-as-indacene 1.1 tert-butyl thiazol-5-ylcarbamate A mixture of DPPA (31.1 g, 113 mmol), Et$_3$N (23.70 mL, 170 mmol) and thiazole-5-carboxylic acid (8.0 g, 61.9 mmol) in tert-BuOH (190 mL) was heated to 90° C. for 12 h in a 500 mL round-bottomed flask. After cooling, the solvent was evaporated in vacuo. The residue was diluted with water. The aqueous layer was extracted with ethyl acetate (3×100 mL). The combined organic phase was washed with brine, dried, concentrated under reduced pressure to give crude product. The crude product was purified by column chromatography on silica gel (EA/heptane=1/10) to give the title compound (5.0 g, 24.97 mmol, 40.3%) as a white solid.

LC-MS: m/z 201 (M+H), RT=1.74 min.

1.2 thiazol-5-amine hydrochloride

To a solution of tert-butyl thiazol-5-ylcarbamate from example 1.1 (20 g, 100 mmol) in methanol (100 mL) was added HCl/dioxane (50 mL). The solution was stirred at room temperature for 2 h. The solution was concentrated to give the title compound as a pale yellow solid (10.9 g, 0.80 mmol, 80%). It was used directly for next step without further purification.

LC-MS: m/z 137 (M+H), RT=0.05 min 1.3 N-(thiazol-5-yl)acetamide

To a solution of Et$_3$N (0.31 mL, 2.20 mmol) and thiazol-5-amine hydrochloride (0.2 g, 1.46 mmol) from example 1.2 in DCM (10 mL) was added Ac$_2$O (0.21 mL, 2.20 mmol). The mixture was stirred at room temperature for 3 h and then concentrated. The resulting mixture was deposited onto silica gel and loaded onto a silica gel column and eluted with EA to give the title compound (0.14 g, 0.98 mmol, 70%).

LC-MS: m/z 143 (M+H), RT=0.83 min 1.4 N-(2,4-dibromothiazol-5-yl)acetamide

To a solution of N-(thiazol-5-yl)acetamide from example 1.3 (0.5 g, 3.52 mmol) in CHCl$_3$ (30 mL) was added bromine (0.36 mL, 7.03 mmol). The solution was stirred at room temperature for 12 h to give a brown solution. The reaction mixture was diluted with saturated NaHSO$_3$. The aqueous layer was extracted with DCM (3×15 mL). The combined organic layers were washed with brine, dried with Na$_2$SO4, filtered and concentrated to afford a yellow solid. The resulting mixture was deposited onto silica gel and loaded onto a silica gel column and eluted with PE/EA(1:1) to give the title compound (0.70 g, 2.33 mmol, yield 66.4%) as a yellow solid.

LC-MS: m/z 300 (M+H), RT=1.80 min

1.5 N-(4-bromothiazol-5-yl)acetamide

A mixture of N-(2,4-dibromothiazol-5-yl)acetamide from example 1.4 (0.35 g, 1.17 mmol), diethylamine (0.085 g, 1.17 mmol) and Raney Ni (0.14 g, 2.33 mmol) in ethanol (50 mL) was stirred at room temperature for 12 h in a 100 mL round-bottomed flask to give a black solution. The reaction mixture was filtered and concentrated to give the title compound (0.20 g, 0.91 mmol, 78%) as a yellow solid which was directly used for the next step without purification.

LC-MS: m/z 222 (M+H), RT=1.30 min

1.6 4-methyl-2-propyl-1H-imidazole

A mixture of butyraldehyde (5.0 g, 69.3 mmol) and ammonium hydroxide (15 mL, 385 mmol) in ethanol (15 mL) was stirred at 60° C. in a 50 mL round-bottomed flask. A solution of 2-oxopropanal (25.0 g, 104 mmol) was added. The mixture was stirred for 12 h. The reaction mixture was diluted with water. The aqueous layer was extracted with ethyl acetate (3×50 mL). The combined organic layers were washed with brine, dried with Na$_2$SO$_4$, filtered and concentrated to afford a yellow solution. The resulting mixture was deposited onto silica gel and loaded onto a silica gel column and eluted with PE/EA(1:1) to give the title compound (5.6 g, 45.1 mmol, 65%) as a brown liquid.

LC-MS: m/z 125 (M+H), RT=1.39 min;
$^1$H NMR (400 MHz, CDCl$_3$): δ=10.46 (s, 1H), 8.60 (s, 1H), 2.67 (t, J=8.0 Hz, 2H), 2.20 (s, 3H), 1.74-1.69 (m, 2H), 0.92 (t, J=7.2 Hz, 3H).

1.7 N-(4-(4-methyl-2-propyl-1H-imidazol-1-yl)thiazol-5-yl)acetamide

A flask was charged with 4-methyl-2-propyl-1H-imidazole from example 1.6 (140 mg, 1.13 mmol), Cs$_2$CO$_3$ (1.10 g, 3.39 mmol) and copper (I) iodide (108 mg, 0.56 mmol). A solution of (1R,2R)-N1,N2-dimethylcyclohexane-1,2-diamine (80 mg, 0.56 mmol,) and N-(4-bromothiazol-5-yl)acetamide from example 1.5 (250 mg, 1.13 mmol) in DMF (30 mL) was added under N$_2$. The mixture was heated at 90° C. for overnight. It was concentrated and directly used for the next step without further purification.

LC-MS: m/z 265 (M+H), RT=1.58 min.

1.8 5,6-Dimethyl-8-propyl-3-thia-1,4,7,8a-tetraaza-as-indacene

To a solution of N-(4-(4-methyl-2-propyl-1H-imidazol-1-yl)thiazol-5-yl)acetamide from example 1.7 (10 mg, 0.038 mmol) in POCl$_3$ (3 mL) was quickly added phosphorus P$_2$O$_5$ (10.74 mg, 0.076 mmol). The reaction mixture was refluxed at 110° C. for 4 h. POCl$_3$ was evaporated and the residue was carefully quenched with ice-water. The mixture was neutralized with saturated Na$_2$CO$_3$ solution and extracted with ethyl acetate (3×30 mL). The combined organic layer was washed with brine and concentrated to give brown liquid and then purified by pre-HPLC to give the title compound (5 mg, 0.02 mmol, 53.7%) as a white solid.

LC-MS: m/z 246 (M+H), RT=2.41 min;
$^1$H NMR (400 MHz, CDCl$_3$): δ=8.88 (s, 1H), 4.77 (s, 1H), 3.30 (t, J=7.6 Hz, 2H), 2.67 (s, 3H), 2.63 (s, 3H), 1.70-1.75 (m, 2H), 0.89 (t, J=7.6 Hz, 3H).

Example 2

5,6-Dimethyl-8-propyl-1-thia-3,4,7,8a-tetraaza-as-indacene

2.1 tert-butyl thiazol-4-ylcarbamate

DPPA (1.19 g, 4.34 mmol) was added dropwise to a mixture of thiazole-4-carboxylic acid (0.5 g, 3.87 mmol) and triethylamine (0.44 g, 4.30 mmol) in tert-BuOH (50 mL) at 0° C.-5° C. The mixture was heated to 90° C. for overnight. The solvent was evaporated in vacuo, the residue was diluted with water and extracted with EA (3×20 mL). The combined organic phase was washed with brine, dried with Na$_2$SO$_4$, concentrated under reduced pressure to give crude product. The crude product was purified by column chromatography on silica gel (EA/heptane=1/10) to give the title compound (0.47 g, 2.35 mmol, 60.6%) as a white solid.

LC-MS: m/z 201 (M+H), RT=1.28 min;
$^1$H NMR (400 MHz, CDCl$_3$): δ=8.59 (d, J=2.4 Hz, 2H), 7.31 (s, 1H), 1.54 (s, 9H).

2.2 thiazol-4-amine hydrochloride

To a solution of tert-butyl 5-iodothiazol-4-ylcarbamate (0.80 g, 3.99 mmol) in DCM (10 mL) was added HCl/dioxane (5 mL). The solution was stirred at room temperature for 2 h. The solution was concentrated to give a pale yellow solid (0.40 g, 4.0 mmol, 73%). It was used directly for next step without purification.

LC-MS: m/z 101 (M+H), RT=0.4 min

2.3 N-(thiazol-4-yl)acetamide

Acetic anhydride (153 mg, 1.50 mmol) was added to the solution of thiazol-4-amine hydrochloride from example 2.2 (100 mg, 1.0 mmol) and triethylamine (152 mg, 1.50 mmol) in DCM (5 mL). The solution was stirred for overnight at room temperature. The reaction mixture was diluted with water, washed with 0.1 M HCl (10 mL), NaHCO$_3$ solution and brine. The combined organic layers were dried with Na$_2$SO$_4$, filtered and concentrated. The resulting mixture was deposited onto silica gel and loaded onto a silica gel column and eluted with EA/PE (1:2) to aim product (55 mg, 0.39 mmol, 38.7%).

LC-MS: m/z 143 (M+H), RT=0.94 min;
$^1$H NMR (400 MHz, CDCl$_3$): δ=8.63 (s, 1H), 8.59 (d, J=2.0 Hz, 1H), 7.71 (d, J=2.4 Hz, 1H), 2.21 (s, 3H).

2.4 N-(5-bromothiazol-4-yl)acetamide

1-Bromopyrrolidine-2,5-dione (0.48 g, 2.67 mmol) was added to the solution of N-(thiazol-4-yl)acetamide (0.38 g, 2.67 mmol) in AcOH/THF (10 mL/10 mL). The mixture was heated to 25° C. for 2 h. The solvent was removed and the solution was adjusted to pH~9 with 2 N NaOH solution. It was extracted with EA (3×50 mL), the combined organic phase was washed with brine, dried with Na$_2$SO$_4$ and concentrated to give the title compound (1.32 g, 1.45 mmol, 54.2%) as light yellow solid.

LC-MS: m/z 222 (M+H), RT=0.97 min;
$^1$H NMR (400 MHz, CDCl$_3$): δ=8.73 (s, 1H), 7.32 (s, 1H), 2.24 (s, 3H).

2.5 N-(5-(4-methyl-2-propyl-1H-imidazol-1-yl)thiazol-4-yl)acetamide

N-(5-bromothiazol-4-yl)acetamide from example 2.4 (0.27 g, 1.22 mmol), potassium carbonate (0.17 g, 1.221 mmol) and 4-methyl-2-propyl-1H-imidazole from example 1.6 (0.15 g, 1.22 mmol) were added sequentially to dioxane (30 mL). The mixture was heated to 100° C. for 18 h. It was purified by pre-HPLC to give the title compound (3 mg, 0.01 mmol, 10%) as a white solid.
LC-MS: m/z 265 (M+H), RT=1.20 min;

2.6 5,6-Dimethyl-8-propyl-1-thia-3,4,7,8a-tetraaza-as-indacene

N-(5-(4-methyl-2-propyl-1H-imidazol-1-yl)thiazol-4-yl)acetamide from example 2.5 (8 mg, 0.030 mmol) and phosphorus pentoxide (21.48 mg, 0.15 mmol) were added sequentially quickly to POCl$_3$ (5 mL). The mixture was heated to 110° C. for 4 h, POCl$_3$ was evaporated and the residue was quenched with ice-water. The mixture was neutralized with saturated Na$_2$CO$_3$ solution and extracted with EA (3×20 mL). The combined organic layer was washed with brine and concentrated to give brown liquid. It was purified by pre-HPLC to give the title compound (5.0 mg, 0.02 mmol, 67.1%) as a white solid.
LC-MS>: m/z 247 (M+H), RT=1.32 min;
$^1$H NMR (400 MHz, CDCl$_3$): δ=8.76 (s, 1H), 3.10 (t, J=7.6 Hz, 2H), 2.86 (s, 3H), 2.78 (s, 3H), 1.87-1.93 (m, 2H), 1.08 (t, J=7.2 Hz, 3H).

Example 3

2,5,6-Trimethyl-8-propyl-3-thia-1,4,7,8a-tetraaza-as-indacene

3.1 tert-butyl 2-methylthiazol-5-ylcarbamate

To a solution of 1,3-thiazole-5-carboxylic acid (5 g, 34.9 mmol) in tert-BuOH (100 mL) was added Et$_3$N (3.92 g, 38.8 mmol) and DPPA (10.7 g, 39.1 mmol) and the resulting solution was heated to reflux for 8 hours. After cooling, the solvent was removed and the residue was added water (50 mL) and extracted with EA (3*100 mL). The combined organic phase was washed with brine, dried (Na$_2$SO$_4$), concentrated and purified by silica gel column (PE:EA=1:1) to give the title compound as a white solid (3.9 g, 54% yield).
LC-MS: m/z 215 (M+H), RT=0.94 min.

3.2 2-methylthiazol-5-amine hydrochloride

To a solution of tert-butyl 2-methylthiazol-5-ylcarbamate from example 3.1 (3 g, 14 mmol) in methanol (10 mL) was added HCl/dioxane (20 mL, 4 mol/L). The solution was stirred at room temperature for 2 hr. The solution was concentrated to give the title compound as a yellow solid (2.3 g, yield: 95%). The title compound was directly used for the next step without further purification.
LC-MS: m/z 115 (M+H), RT=0.52 min.

3.3 N-(2-methylthiazol-5-yl)acetamide

To a solution of Et$_3$N (1.4 ml, 10 mmol) and 2-methylthiazol-5-amine hydrochloride (1 g, 6.6 mmol) in DCM (30 mL) was added Ac$_2$O (0.94 mL, 10 mmol). The mixture was stirred at room temperature for 3 h. The reaction solution was concentrated, deposited onto silica gel and loaded onto a silica gel column and eluted with EA to give the title compound (0.8 g, yield: 77%).
LC-MS: m/z 157 (M+H), RT=1.07 min

3.4 N-(4-bromo-2-methylthiazol-5-yl)acetamide

To a solution of N-(2-methylthiazol-5-yl)acetamide (0.4 g, 2.6 mmol) in CHCl$_3$ (30 mL) was added Br$_2$ (0.15 mL, 2.8 mmol), then the solution was stirred at room temperature for 12 h to give a brown solution. The reaction mixture was diluted with saturated NaHSO$_3$ solution. The aqueous layer was extracted with DCM (3×30 mL). The combined organic layers were dried with Na$_2$SO4, filtered and concentrated to afford a yellow solid. The resulting mixture was deposited onto silica gel and loaded onto a silica gel column and eluted with PE/EA(1:1) to give the title compound (400 mg, yield 67%).
LC-MS: m/z 235 (M+H), RT=1.21 min;
$^1$H NMR (400 MHz, CDCl$_3$): δ=8.6 (s, 1H), 2.53 (s, 3H), 2.21 (s, 3H)

3.5 N-(2-methyl-4-(4-methyl-2-propyl-1H-imidazol-1-yl)thiazol-5-yl)acetamide A flask (backfilled with N$_2$) was charged with N-(4-bromo-2-methylthiazol-5-yl)acetamide (400 mg, 1.7 mmol), CuI(324 mg, 1.7 mmol) and Cs$_2$CO$_3$ (1.6 g, 5.1 mmol). Trans-N,N'-dimethylcyclohexane-1,2-diamine (CAS: 61798-24-1, 242 mg, 1.7 mmol) and 4-methyl-2-propyl-1H-imidazole (230 mg, 1.9 mmol) in DMF (9.0 mL) were added and the mixture was stirred at 90° C. overnight. After the mixture was cooled to room temperature, the mixture was filtered through a syringe filter (washed with DMF). The filtrate was purified by prep-HPLC to give 60 mg of the pure title compound.
LC-MS: m/z 235 (M+H), RT=1.21 min

3.6 2,5,6-trimethyl-8-propyl-3-thia-1,4,7,8a-tetraaza-as-indacene

N-(2-methyl-4-(4-methyl-2-propyl-1H-imidazol-1-yl)thiazol-5-yl)acetamide (60 mg, 0.2 mmol) was suspended in phosphorus oxychloride (5 mL) and P$_2$O$_5$ (280 mg, 2 mmol) was added quickly. The resulting mixture was heated at 130° C. in a sealed tube overnight. After POCl$_3$ was evaporated, the residue was quenched with ice water very carefully. The mixture was neutralized with saturated Na$_2$CO$_3$ solution and extracted with ethyl acetate (3×30 mL). The organic layer was dried over Na$_2$SO$_4$, concentrated and purified by prep-HPLC to give 4 mg of the title compound.
LC-MS: m/z 261 (M+H), RT=1.67 min;
$^1$H NMR (400 MHz, CDCl$_3$): δ=3.44 (t, J=8.0 Hz, 2H), 2.80 (s, 3H), 2.78 (s, 3H), 2.76 (s, 3H), 1.90-1.85 (m, 2H), 1.03 (t, J=7.2 Hz, 3H)

Example 4

2-Bromo-5,6-dimethyl-8-propyl-3-thia-1,4,7,8a-tetraaza-as-indacene

To a solution of 5,6-dimethyl-8-propyl-3-thia-1,4,7,8a-tetraaza-as-indacene from example 1 (40 mg, 0.16 mmol) in CHCl$_3$ (10 mL) was added Br$_2$ (78 mg, 0.5 mmol), then the solution was stirred at room temperature overnight to give a brown solution. LC-MS showed 30% of the title compound and 35% of 5,6-dimethyl-8-propyl-3-thia-1,4,7,8a-tetraaza-as-indacene. The reaction mixture was diluted with sat. $NaHSO_3$ solution. The aqueous layer was extracted with DCM (3×10 mL). The combined organic layers were dried with $Na_2SO_4$, filtered and concentrated.

LC-MS: m/z 325 (M+H), RT=1.59 min.

Example 5

2-Methoxy-5,6-dimethyl-8-propyl-3-thia-1,4,7,8a-tetraaza-as-indacene

2-Bromo-5,6-dimethyl-8-propyl-3-thia-1,4,7,8a-tetraaza-as-indacene was dissolved in 5 mL of methanol and sodium methoxide (4.98 mg, 0.092 mmol) was added. The resulting mixture was stirred at 60° C. for 1 h. LC-MS showed complete consumption of 2-bromo-5,6-dimethyl-8-propyl-3-thia-1,4,7,8a-tetraaza-as-indacene. After removal of the solvent under reduced pressure, 5 mL of water and 10 mL of EA were added. The organic layer was concentrated, crude product was purified by prep-HPLC to give 4 mg of the title compound.

LC-MS: m/z 277 (M+H), RT=1.70 min;
$^1$H NMR (400 MHz, $CDCl_3$): δ=4.20 (s, 3H), 3.40 (t, J=7.6 Hz, 2H), 2.78 (s, 3H), 2.77 (s, 3H), 1.88-1.86 (m, 2H), 1.04 (t, J=7.2 Hz, 3H).

Example 6

5,6-Dimethyl-3-thia-1,4,7,8a-tetraaza-as-indacene 6.1 N-(4-(4-methyl-1H-imidazol-1-yl)thiazol-5-yl)acetamide N-(4-bromothiazol-5-yl)acetamide from example 1.5 (1 g, 4.52 mmol), CuI(869 mg, 4.52 mmol) and $Cs_2CO_3$ (2.9 g, 9.1 mmol) were combined in a flask (backfilled with $N_2$). Trans-N,N'-dimethylcyclohexane-1,2-diamine (630 mg, 4.52 mmol) and 4-methyl-1H-imidazole (446 mg, 5.4 mmol) in DMF (10 mL) were added and the mixture was stirred at 90° C. overnight. After the mixture was cooled to room temperature, the mixture was filtered through a syringe filter (washed with DMF). The filtrate purified by prep-HPLC to give 200 mg of the pure title compound (yield: 20%).

LC-MS: m/z 223 (M+H), RT=1.12 min;
$^1$H NMR (400 MHz, $CDCl_3$): δ=12.73 (s, 1H), 8.34 (s, 1H), 2.31 (s, 3H), 2.02 (s, 3H)

6.2 5,6-dimethyl-3-thia-1,4,7,8a-tetraaza-as-indacene

N-(4-(4-methyl-1H-imidazol-1-yl)thiazol-5-yl)acetamide (50 mg, 0.23 mmol) was suspended in phosphorus oxychloride (5 mL) and $P_2O_5$ (326 mg, 2.3 mmol) was added quickly. The resulting mixture was heated at 160° C. in a sealed tube for 24 hr. After $POCl_3$ was evaporated, the residue was quenched with ice water very carefully. The mixture was neutralized with saturated $Na_2CO_3$ solution and extracted with ethyl acetate. The organic layer was dried over $Na_2SO_4$, concentrated (the crude product can also be directly used for next step), purified by prep-HPLC to give 15 mg of the title compound (yield: 33%).

LC-MS: m/z 205 (M+H), RT=1.29 min;
$^1$H NMR (400 MHz, $CDCl_3$): δ=8.78 (s, 1H), 8.67 (s, 1H), 2.87 (s, 3H), 2.82 (s, 3H)

Example 7

8-Bromo-5,6-dimethyl-3-thia-1,4,7,8a-tetraaza-as-indacene 5,6-dimethyl-3-thia-1,4,7,8a-tetraaza-as-indacene (300 mg, 1.469 mmol) was dissolved in acetonitrile (50 ml) and 1-bromopyrrolidine-2,5-dione (131 mg, 0.734 mmol) was added. The resulting mixture was stirred at about 20° C. for about 1 h. After removal of the solvent under reduced pressure, the crude product was purified by prep-HPLC to give 60 mg of the title compound (yield: 15%).

LC-MS: m/z 285 (M+H), RT=1.53 min;
$^1$H NMR (400 MHz, $CDCl_3$): δ=8.84 (s, 1H), 2.83 (s, 3H), 2.80 (s, 3H)

Example 8

3-(5,6-Dimethyl-3-thia-1,4,7,8a-tetraaza-as-indacen-8-yl)-benzamide

Under argon atmosphere, a 5 mL microwave reaction vial was charged with 8-bromo-5,6-dimethyl-3-thia-1,4,7,8a-tetraaza-as-indacene from example 7 (10 mg, 0.035 mmol), 3-carbamoylphenylboronic acid (9 mg, 0.053 mmol) and $Cs_2CO_3$ (23 mg, 0.071 mmol) in DMF (3 mL) followed by the addition of $Pd(dppf)Cl_2$ (3 mg, 3.5 µmol). The resulting suspension was heated on microwave at 100° C. for 1 hr. The reaction mixture was filtered and the filtrate was purified by Prep-HPLC to give the title compound (6 mg, yield: 52%) as a white solid.

LC-MS: m/z 324 (M+H), RT=1.31 min;
$^1$H NMR (400 MHz, DMSO): δ=9.10 (s, 1H), 8.34 (s, 1H), 8.03 (s, 1H), 8.80-7.97 (m, 2H), 7.58 (t, J=7.6 Hz, 1H), 7.43 (s, 1H), 2.86 (s, 3H), 2.80 (s, 3H)

The compounds of examples 9-11 were prepared following the same way shown in example 8.

Example 9

5,6-Dimethyl-8-(2-methyl-pyridin-3-yl)-3-thia-1,4,7,8a-tetraaza-as-indacene

LC-MS: m/z 296 (M+H), RT=1.34 min;
$^1$H NMR (400 MHz, DMSO): δ=9.03 (s, 1H), 8.60-8.58 (m, 1H), 7.86-7.83 (m, 1H), 7.36-7.33 (m, 1H), 2.87 (s, 3H), 2.80 (s, 3H), 2.22 (s, 3H)

Example 10

5,6-Dimethyl-8-(2-methyl-pyridin-4-yl)-3-thia-1,4,7,8a-tetraaza-as-indacene

LC-MS: m/z 296 (M+H), RT=1.40 min;
$^1$H NMR (400 MHz, DMSO): δ=9.17 (s, 1H), 8.56 (d, J=4.8 Hz, 1H), 7.75 (s, 1H), 7.71 (d, J=5.2 Hz, 1H), 2.87 (s, 3H), 2.80 (s, 3H), 2.55 (s, 3H)

Example 11

5,6-Dimethyl-8-(6-methyl-pyridin-3-yl)-3-thia-1,4,7,8a-tetraaza-as-indacene

LC-MS: m/z 296 (M+H), RT=1.39 min;
$^1$H NMR (400 MHz, DMSO): δ=9.13 (s, 1H), 8.95 (d, J=2.4 Hz, 1H), 8.15 (d, J=2.4 Hz, 1H), 7.39 (d, J=8.0 Hz, 1H), 2.85 (s, 3H), 2.79 (s, 3H), 2.56 (s, 3H)

II. Biological Tests a) Measurement of PDE Activity

The recombinant PDE proteins are used in in vitro enzymatic reaction for measurement of PDE activity. These recombinant proteins, including PDE10A (human, rat and mouse PDE10) and isoforms of PDEs 1, 3, 4, and 5, were purchased from commercial vendor BPS Bioscience. The enzymatic activity of PDEs was determined by cAMP measurement kit from CisBio (IBA) using HTRF technology.

The PDE enzymatic reaction was carried out in assay buffer (20 mM Tris-HCl pH7.5, 10 mM $MgCl_2$, 0.1% bovine serum albumin) containing enzyme and substrate. The PDE enzymes concentration ranged from 10 pM-250 pM, depending on each enzyme's specific activity. The substrate cyclic nucleotide (cAMP or cGMP) concentration used in the assay was 20 nM for PDE10, and 100 nM for other PDEs. The inhibitory effect of compound was determined by incubating various concentration of inhibitor in the enzymatic assay. Typically, compound was serial diluted in DMSO then further diluted in assay buffer. Next, the compound at varying concentration was mixed with PDE enzyme. The reaction was initiated by addition of cyclic nucleotide substrate, and incubated for 60 minutes at 29 C. The reaction was stopped by addition of lysis buffer from assay kit. The cAMP-d2 and anti-cAMP cryptate in the lysis buffer detected the level of cAMP left from the PDE hydrolysis reaction. The PDE activity is reversely correlated with the amount of cAMP left in the reaction and can be converted to the percent activity of an uninhibited control (100%). Thus, $IC_{50}$ value of inhibitor can be obtained by plotting inhibitor concentration against PDE activity at that concentration. The results are shown in Table 1.

TABLE 1

| EXAMPLE | $IC_{50}$ |
|---|---|
| 1 | ++ |
| 3 | +++ |
| 5 | +++ |
| 8 | +++ |
| 9 | +++ |
| 10 | ++ |

1) +++: $IC_{50}$ < 100 nM ++: 100 nM ≤ $IC_{50}$ ≤ 200 nM +: 200 nM < $IC_{50}$ < 500 nM b) Determination of the Microsomal Half-life:

The metabolic stability of the compounds of the invention was determined in the following assay.

The test substances were incubated in a concentration of 0.5 μM as follows:

0.5 μM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 μl aliquots are removed, and the reaction is immediately stopped and cooled with the same volume of acetonitrile. The samples are frozen until analyzed. The remaining concentration of undegraded test substance is determined by MSMS. The half-life (T½) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln 2/T½/(content of microsomal protein in mg/ml)×1000 [ml/min/mg] (modified from references: Di, The Society for Bimolecular Screening, 2003, 453-462; Obach, D M D, 1999 vol 27. N 11, 1350-1359). The results are shown in Table 2.

TABLE 2

| Ex. | Rat mCl[2] [μl $min^{-1}$ $mg^{-1}$] | Human mCl[2] [μl $min^{-1}$ $mg^{-1}$] |
|---|---|---|
| 1 | + | ++ |
| 3 | ○ | + |
| 5 | ○ | ○ |
| 8 | ++ | ++ |
| 9 | ++ | ++ |
| 11 | + | + |

Ex. EXAMPLE
mCl microsomal clearance
[2] ++: <100 μl $min^{-1}$ $mg^{-1}$ +: 100-220 μl $min^{-1}$ $mg^{-1}$ ○: >220 μl $min^{-1}$ $mg^{-1}$

We claim:

1. A compound of formula I

(I)

where in formula I the variables X, Y, $Q^1$, $Q^2$, $R^1$ and $R^2$ have the following meanings:

X is C—$R^3$ or N;

$Q^1$ is S or O and $Q^2$ is C—$R^4$ or N and $Q^2$ is connected to X via a double bond while $Q^1$ is connected to X via a single bond; or $Q^2$ is S or O and $Q^1$ is C—$R^4$ or N and $Q^1$ is connected to X via a double bond while $Q^2$ is connected to X via a single bond;

Y is C—$R^5$;

$R^1$ is selected from the group consisting of hydrogen, halogen, cyano, nitro, $R^{11}$, OH, $OR^{12}$, $S(O)_qR^{13}$, C(O)H, C(O)$R^{14}$, C(O)OH, C(O)$OR^{15}$, OC(O)$R^{16}$, $Y^1$—$NR^{17}R^{18}$, $Y^1$—N($R^{19}$)—$Y^3$—$NR^{17}R^{18}$, $Y^1$—N($R^{19}$)—$Y^2$—$R^{15a}$, and a moiety $Z^1$—$Ar^1$;

$R^2$ is selected from the group consisting of hydrogen, halogen, cyano, nitro, $R^{21}$, OH, $OR^{22}$, $S(O)_qR^{23}$, C(O)H, C(O)$R^{24}$, C(O)OH, C(O)$OR^{25}$, OC(O)$R^{26}$, $Y^1$—$NR^{27}R^{28}$, $Y^1$—N($R^{29}$)—$Y^3$—$NR^{27}R^{28}$, $Y^1$—N($R^{19}$)—$Y^2$—$R^{25a}$, and a moiety $Z^2$—$Ar^2$;

provided that at least one of $R^1$ and $R^2$ is different from hydrogen;

$R^3$ is selected from the group consisting of hydrogen, halogen, cyano, nitro, $R^{31}$, $OR^{32}$, $S(O)_qR^{33}$, C(O)H, C(O)$R^{34}$, C(O)OH, C(O)$OR^{35}$, OC(O)$R^{36}$, $Y^1$—$NR^{37}R^{38}$, $Y^1$—N($R^{39}$)—$Y^3$—$NR^{37}R^{38}$, $Y^1$—N($R^{39}$)—$Y^2$—$R^{35a}$, and a moiety $Z^3$—$Ar^3$;

$R^4$ is selected from the group consisting of hydrogen, halogen, cyano, nitro, $R^{41}$, $OR^{42}$, $S(O)_qR^{43}$, C(O)H, C(O)$R^{44}$, C(O)OH, C(O)$OR^{45}$, OC(O)$R^{46}$, $Y^1$—$NR^{47}R^{48}$, $Y^1$—N($R^{49}$)—$Y^3$—$NR^{47}R^{48}$, $Y^1$—N($R^{49}$)—$Y^2$—$R^{45a}$, and a moiety $Z^4$—$Ar^4$;

$R^5$ is selected from the group consisting of hydrogen, halogen, cyano, nitro, $R^{51}$, $OR^{52}$, $S(O)_qR^{53}$, C(O)H, C(O)$R^{54}$, C(O)OH, C(O)$OR^{55}$, OC(O)$R^{56}$, $Y^1$—$NR^{57}R^{58}$, $Y^1$—N($R^{59}$)—$Y^3$—$NR^{57}R^{58}$, $Y^1$—N($R^{59}$)—$Y^2$—$R^{55a}$, and a moiety $Z^5$—$Ar^5$;

$R^{11}, R^{12}, R^{13}, R^{14}, R^{15}, R^{16}, R^{21}, R^{22}, R^{23}, R^{24}, R^{25}, R^{26},$ $R^{31}, R^{32}, R^{33}, R^{34}, R^{35}, R^{36}, R^{41}, R^{42}, R^{43}, R^{44}, R^{45},$ $R^{46}, R^{51}, R^{52}, R^{53}, R^{54}, R^{55}$, and $R^{56}$, independently of each other, are selected from the group consisting of $C_1$-$C_8$-alkyl, $C_2$-$C_8$-alkenyl, $C_2$-$C_8$-alkynyl, $C_3$-$C_8$-cycloalkyl, $C_5$-$C_8$-cycloalkenyl, and $C_3$-$C_8$-cycloalkyl-$C_1$-$C_4$ alkyl, where the 6 aforementioned substituents may be unsubstituted, partially or completely halogenated or carry 1, 2 or 3 radicals $R^y$, and C-bound 5- to 8-membered heterocyclyl, which is saturated or partially unsaturated and has 1 or 2 heteroatom moieties as ring members, which are selected from the group consisting of O, N, S, S(O), S(O)$_2$, and N—$R^x$, where heterocyclyl is unsubstituted or carries 1, 2, 3 or 4 radicals $R^{yy}$;

$R^{17}$ and $R^{18}$, independently of each other, are selected from the group consisting of hydrogen, tri-$C_1$-$C_4$-alkylsilyl, $C_1$-$C_8$-alkyl, $C_2$-$C_8$-alkenyl, $C_2$-$C_8$-alkynyl, $C_3$-$C_8$-cycloalkyl, $C_5$-$C_8$cycloalkenyl, $C_3$-$C_8$-cycloalkyl $C_1$-$C_4$ alkyl, where the 6 aforementioned substituents may be unsubstituted, partially or completely halogenated or carry 1, 2 or 3 radicals $R^y$, $C_1$-$C_8$-alkylcarbonyl, $C_1$-$C_4$-haloalkylcarbonyl, $C_1$-$C_8$-alkylsulfonyl, $C_1$-$C_4$-haloalkylsulfonyl, and C-bound 5- to 8-membered heterocyclyl, which is saturated or partially unsaturated and has 1 or 2 heteroatom moieties as ring members, which are selected from the group consisting of O, N, S, S(O), S(O)$_2$, and N—$R^x$, where heterocyclyl is unsubstituted or carries 1, 2, 3 or 4 radicals $R^{yy}$ or $R^{17}$ and $R^{18}$, together with the nitrogen atom, to which they are attached, form an N-bound 5- to 8-membered heterocyclyl, which is saturated, partially unsaturated or aromatic and in addition to the nitrogen atom may have 1 or 2 further heteroatom moieties as ring members, which are selected from the group consisting of O, N, S, S(O), S(O)$_2$, and N—$R^x$, where heterocyclyl is unsubstituted or carries 1, 2, 3 or 4 radicals $R^{yy}$;

$R^{19}, R^{29}, R^{39}, R^{49}$ and $R^{59}$, independently of each other, are hydrogen or have one of the meanings given for $R^{11}$;

$R^{27}$ and $R^{28}$ are as defined for $R^{17}$ and $R^{18}$;
$R^{37}$ and $R^{38}$ are as defined for $R^{17}$ and $R^{18}$;
$R^{47}$ and $R^{48}$ are as defined for $R^{17}$ and $R^{18}$;
$R^{57}$ and $R^{58}$ are as defined for $R^{17}$ and $R^{18}$;
$R^{15a}, R^{25a}, R^{35a}, R^{45a}$ and $R^{55a}$, independently of each other, have one of the meanings given for $R^{11}$;
q is 0, 1, or 2
$Ar^1, Ar^2, Ar^3, Ar^4$ and $Ar^5$, independently of each other, are selected from the group consisting of aryl, monocyclic 5- or 6-membered hetaryl, and bicyclic 9 or 10 membered hetaryl, where hetaryl has 1, 2 or 3 heteroatoms as ring members which are selected from the group consisting of O, S, and N, where aryl and hetaryl are unsubstituted or carry 1, 2, 3 or 4 identical or different substituents $R^{Ar}$;
$Y^1$ is a single bond, $C_1$-$C_4$-alkylene, $Y^5$—O—$Y^6$, $Y^5$—S(O)$_q$—$Y^6$, $Y^5$—C(O)—$Y^6$, $Y^5$—C(S)—$Y^6$, $Y^5$—C(O)O—$Y^6$, $Y^5$—OC(O)—$Y^6$, or $Y^5$—N($R^z$)—$Y^4$;
$Y^2$ is a single bond, $C_1$-$C_4$-alkylene, $Y^5$—O—$Y^6$, $Y^5$—S(O)$_q$—$Y^6$, $Y^5$—C(O)—$Y^6$, $Y^5$—C(S)—$Y^6$, $Y^5$—C(O)O—$Y^6$, $Y^5$—OC(O)—$Y^6$, or $Y^5$—N($R^z$)—$Y^4$;
$Y^3$ is a single bond, $C_1$-$C_4$-alkylene, $Y^5$—S(O)$_q$—$Y^6$, $Y^5$—C(O)—$Y^6$, $Y^5$—C(S)—$Y^6$, $Y^5$—C(O)O—$Y^6$, or $Y^5$—OC(O)—$Y^6$;
$Y^4$ is a $C_1$-$C_4$-alkylene, $Y^5$—S(O)$_q$—$Y^6$, $Y^5$—C(O)—$Y^6$, $Y^5$—C(S)—$Y^6$, $Y^5$—C(O)O—$Y^6$, or $Y^5$—OC(O)—$Y^6$;
$Y^5$ is a single bond or $C_1$-$C_4$-alkylene;
$Y^6$ is a single bond or $C_1$-$C_4$-alkylene;
$Z^1, Z^2, Z^3, Z^4$ and $Z^5$, independently of each other, are selected from the group consisting of a single bond, $C_1$-$C_4$-alkylene, $Y^5$—O—$Y^6$, $Y^5$—S(O)$_q$—$Y^6$, $Y^5$—C(O)—$Y^6$, $Y^5$—C(S)—$Y^6$, $Y^5$—C(O)O—$Y^6$, $Y^5$—OC(O)—$Y^6$, and $Y^5$—N($R^z$)—$Y^4$;
$R^x$ is selected from the group consisting of hydrogen, $C_1$-$C_8$-alkyl, $C_2$-$C_8$-alkenyl, $C_2$-$C_8$-alkynyl, $C_3$-$C_8$-cycloalkyl, $C_5$-$C_8$-cycloalkenyl, $C_3$-$C_8$-cycloalkyl-$C_1$-$C_4$-alkyl, where the 6 aforementioned substituents may be unsubstituted, partially or completely halogenated or carry 1, 2 or 3 radicals $R^y$, phenyl and phenyl-$C_1$-$C_4$-alkyl, where phenyl and phenyl-$C_1$-$C_4$-alkyl are unsubstituted or carry 1, 2, 3 or 4 radicals $R^{yy}$;
$R^y$ is selected from the group consisting of cyano, OH, $OR^{y2}$, $S(O)_q R^{y3}$, $C(O)H$, $C(O)R^{y4}$, $C(O)OH$, $C(O)OR^{y5}$, $OC(O)R^{y6}$, $Y^1$—$NR^{y7}R^{y8}$, $Y^1$—$N(R^{y9})$—$Y^3$—$NR^{y7}R^{y8}$, and $Y^1$—$N(R^{y9})$—$Y^2$—$R^{y0}$;
$R^{yy}$ is selected from the group consisting of cyano, halogen, $R^{y1}$, OH, $OR^{y2}$, $S(O)_q R^{y3}$, $C(O)H$, $C(O)R^{y4}$, $C(O)OH$, $C(O)OR^{y5}$, $OC(O)R^{y6}$, $Y^1$—$NR^{y7}R^{y8}$, $Y^1$—$N(R^{y9})$—$Y^3$—$NR^{y7}R^{y8}$, and $Y^1$—$N(R^{y9})$—$Y^2$—$R^{y0}$;
$R^{y0}, R^{y2}, R^{y3}, R^{y4}, R^{y5}$ and $R^{y6}$, independently of each other, are selected from the group consisting of $C_1$-$C_8$-alkyl, $C_2$-$C_8$-alkenyl, $C_2$-$C_8$-alkynyl, $C_3$-$C_8$-cycloalkyl, $C_5$-$C_8$-cycloalkenyl, $C_3$-$C_8$-cycloalkyl-$C_1$-$C_4$-alkyl, and C-bound 5- to 8-membered heterocyclyl, which is saturated or partially unsaturated and has 1 or 2 heteroatom moieties as ring members, which are selected from the group consisting of O, N, S, S(O), S(O)$_2$, NH, and N—($C_1$-$C_4$-alkyl);
$R^{y7}$ and $R^{y8}$ are as defined for $R^{y0}$ or , together with the nitrogen atom, to which they are attached, form an N-bound 5- to 8-membered heterocyclyl, which is saturated or partially unsaturated and in addition to the nitrogen atom may have 1 or 2 further heteroatom moieties as ring members, which are selected from the group consisting of O, N, S, S(O), S(O)$_2$, NH, and N—($C_1$-$C_4$-alkyl), where heterocyclyl is unsubstituted or carries 1, 2, 3 or 4 radicals selected from the group consisting of $C_1$-$C_4$-alkyl;
$R^{y9}$ is hydrogen or has one of the meanings given for $R^{y0}$;
$R^{Ar}$ is selected from the group consisting of halogen, cyano, nitro, OH, $C(O)NH_2$, $R^{Ar1}$, $OR^{Ar2}$, $S(O)_q R^{Ar3}$, $C(O)H$, $C(O)R^{Ar4}$, $C(O)OH$, $C(O)OR^{Ar5}$, $OC(O)R^{Ar6}$, $Y^1$—$NR^{Ar7}R^{Ar8}$, $Y^1$—$N(R^{Ar9})$—$Y^3$—$NR^{Ar7}R^{Ar8}$, and $Y^1$—$N(R^{Ar9})$—$Y^2$—$R^{Ar0}$, where $R^{Ar0}, R^{Ar1}, R^{Ar2}, R^{Ar3}, R^{Ar4}, R^{Ar5}$ and $R^{Ar6}$ have one of the meanings given for $R^{11}$, $R^{Ar7}$ and $R^{Ar8}$ are as defined for $R^{17}$ and $R^{18}$, and $R^{Ar9}$ has one of the meanings given for $R^{19}$;
$R^z$ has one of the meanings given for $R^x$;
or an N-oxide, tautomer, hydrate, or pharmaceutically acceptable salt thereof.

2. The compound of claim 1, where $R^1$ is a radical $R^{11}$ or a moiety $Z^1$—$Ar^1$.

3. The compound of claim 1, where $R^1$ is a moiety $Z^1$—$Ar^1$, where $Z^1$ is a single bond.

4. The compound of claim 1, where $R^1$ is a moiety $Z^1$—$Ar^1$, where $Ar^1$ is selected from the group consisting of phenyl, thienyl, pyrazolyl, isoxazolyl, thialzolyl, 1,2,4-oxadiazolyl and pyridyl, where phenyl, thienyl, pyrazolyl, isoxazolyl, 1,2,4-oxadiazolyl, thialzolyl and pyridyl are unsubstituted or carry 1, 2, 3 or 4 identical or different substituents $R^{Ar}$.

5. The compound of claim 1, where $R^2$ is a radical $R^{21}$, in particular a radical selected from the group consisting of trimethylsilyl, $C_1$-$C_8$-alkyl, $C_3$-$C_8$-cycloalkyl and $C_3$-$C_8$-cycloalkyl-$C_1$-$C_4$-alkyl, where the three last mentioned radicals may be unsubstituted, partially or completely halogenated or where the $C_3$-$C_8$-cycloalkyl radicals may carry 1, 2 or 3 radicals methyl groups and where $R^2$ is especially methyl.

6. The compound of claim 1, where $Q^1$ is N and X is C—$R^3$.

7. The compound of claim 6, where $R^3$ is selected from the group consisting of hydrogen, halogen, $R^{31}$, $OR^{32}$, $C_1$-$C_4$-alkyl, and $C_1$-$C_4$-alkoxy.

8. The compound of claim 6, where $R^3$ is a group $Z^3$—$Ar^3$.

9. The compound of claim 1, where $Q^1$ is C—$R^4$ and X is N.

10. The compound of claim 9, where $R^4$ is selected from the group consisting of hydrogen, halogen, methoxy, methyl, and ethyl.

11. The compound of claim 6, where $Q^2$ is S.

12. The compound of claim 6, where $Q^2$ is O.

13. The compound of claim 1, where $Q^2$ is N and X is C—$R^3$.

14. The compound of claim 13, where $R^3$ is selected from the group consisting of hydrogen, halogen, $R^{31}$, $OR^{32}$, $C_1$-$C_4$-alkyl, and $C_1$-$C_4$-alkoxy.

15. The compound of claim 13, where $R^3$ is a group $Z^3$—$Ar^3$.

16. The compound of claim 1, where $Q^2$ is C—$R^4$ and X is N.

17. The compound of claim 16, where $R^4$ is selected from the group consisting of hydrogen, halogen, methoxy, methyl, and ethyl.

18. The compound of claim 16, where $R^4$ is a group $Z^4$—$Ar^4$.

19. The compound of claim 13, where $Q^1$ is S.

20. The compound of claim 13, where $Q^1$ is O.

21. The compound as claimed in claim 1, where $R^5$ is selected from the group consisting of hydrogen, halogen, a radical $R^{51}$, $CH_2F$, $CHF_2$, $CF_3$, and $CH_2OH$.

22. The compound as claimed in claim 1, where $R^5$ is selected from the group consisting of a radical $Y^1$—$NR^{57}R^{58}$, $Y^1$—$N(R^{59})$—$Y^3$—$NR^{57}R^{58}$, and $Y^1$—$N(R^{59})$—$Y^2$—$R^{55a}$.

23. The compound as claimed in claim 1 which is a compound of the formula I-A

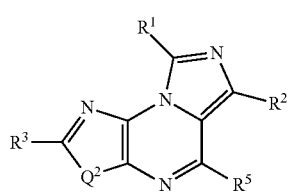

(I-A)

where $Q^2$, $R^1$, $R^2$, $R^3$ and $R^5$ are as defined in claim 1.

24. The compound as claimed in claim 1 which is a compound of the formula I-B

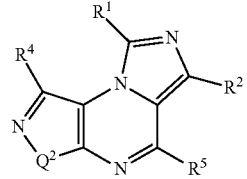

(I-B)

where $Q^2$, $R^1$, $R^2$, $R^4$ and $R^5$ are as defined in claim 1.

25. The compound as claimed in claim 1, which is selected from the group consisting of
5,6-dimethyl-8-(3-nitrophenyl)-3-thia-1,4,7,8a-tetraaza-as-indacene;
5,6-dimethyl-8-(2-methylpyridin-3-yl)-3-thia-1,4,7,8a-tetraaza-as-indacene;
5,6-dimethyl-8-propyl-3-thia-1,4,7,8a-tetraaza-as-indacene;
5,6-dimethyl-8-(3-methylpyridin-4-yl)-3-thia-1,4,7,8a-tetraaza-as-indacene;
5,6-dimethyl-8-(6-methylpyridin-3-yl)-3-thia-1,4,7,8a-tetraaza-as-indacene;
5,6-dimethyl-8-bromo-3-thia-1,4,7,8a-tetraaza-as-indacene;
5,6-dimethyl-3-thia-1,4,7,8a-tetraaza-as-indacene;
2,5,6-trimethyl-8-propyl-3-thia-1,4,7,8a-tetraaza-as-indacene;
2-methoxy-5,6-dimethyl-8-propyl-3-thia-1,4,7,8a-tetraaza-as-indacene;
5,6-Dimethyl-8-propyl-1-thia-3,4,7,8a-tetraaza-as-indacene;
3-(5,6-Dimethyl-3-thia-1,4,7,8a-tetraaza-as-indacen-8-yl)-benzamide; and
5,6-Dimethyl-8-(2-methyl-pyridin-4-yl)-3-thia-1,4,7,8a-tetraaza-as-indacene;
or an N-oxide, tautomer, hydrate, or pharmaceutically acceptable salt thereof.

26. A pharmaceutical composition which comprises a pharmaceutically acceptable carrier and a compound as claimed in claim 1.

27. A method for treating schizophrenia, depression, bipolar disorder, cognitive dysfunction associated with schizophrenia, cognitive dysfunction associated with Alzheimer's disease, Huntington's disease, substance-related disorder, or diet-induced obesity, said method comprising administering an effective amount of at least one compound as claimed in claim 1 to a mammal in need thereof.

28. The method of claim 27, for treating schizophrenia.

29. The method of claim 27, for treating cognitive dysfunction associated with schizophrenia.

30. The method of claim 27, for treating bipolar disorders.

31. The method of claim 27, for treating depression.

32. The method of claim 27, for treating cognitive dysfunction associated with Alzheimer's disease.

33. The method of claim 27, for treating diet-induced obesity.

34. The compound of claim 9, where $Q^2$ is S.

35. The compound of claim 9, where $Q^2$ is O.

36. The compound of claim 16, where $Q^1$ is S.

37. The compound of claim 16, where $Q^1$ is O.